United States Patent
Patti et al.

(10) Patent No.: US 8,815,799 B2
(45) Date of Patent: *Aug. 26, 2014

(54) INHIBITING STRIATED MUSCLE ACTIVATOR OF RHO (STARS) TO IMPROVE GLYCEMIC CONTROL

(75) Inventors: Mary Elizabeth Patti, Newton, MA (US); Wanzhu Jin, Beijing (CN); Allison B. Goldfine, Wayland, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/701,082

(22) PCT Filed: Jun. 3, 2011

(86) PCT No.: PCT/US2011/039059
§ 371 (c)(1),
(2), (4) Date: Mar. 29, 2013

(87) PCT Pub. No.: WO2011/153430
PCT Pub. Date: Dec. 8, 2011

(65) Prior Publication Data
US 2013/0197058 A1    Aug. 1, 2013

Related U.S. Application Data

(60) Provisional application No. 61/351,479, filed on Jun. 4, 2010.

(51) Int. Cl.
*C12N 9/00*    (2006.01)
*C12N 15/82*    (2006.01)
*C12N 15/113*    (2010.01)

(52) U.S. Cl.
CPC .............. *C12N 9/00* (2013.01); *C12N 15/8218* (2013.01); *C12N 15/1137* (2013.01)

USPC ............................. 514/6.9; 514/6.7; 514/6.8

(58) Field of Classification Search
CPC . A61K 31/166; A61K 31/4025; A61K 31/16; A61K 31/7088; A61K 31/713; C07K 14/4702; C12N 15/113; C12N 2310/14
USPC .......................... 514/6.8, 6.9, 6.7, 44 A, 44 R
See application file for complete search history.

(56) References Cited

U.S. PATENT DOCUMENTS

| | | | | |
|---|---|---|---|---|
| 8,003,606 | B2 * | 8/2011 | Patti et al. | 514/5.9 |
| 8,524,661 | B2 * | 9/2013 | Patti et al. | 514/5.9 |
| 2009/0304781 | A1 | 12/2009 | Schaper et al. | |
| 2010/0010074 | A1 | 1/2010 | Patti et al. | |

FOREIGN PATENT DOCUMENTS

WO    2006104751 A2    10/2006

OTHER PUBLICATIONS

Kuwahara, et al., "Muscle-Specific Signaling Mechanism that Links Actin Dynamics to Serum Response Factor", Molecular and Cellular Biology, 2005, vol. 25, No. 8, pp. 3173-3181(10 pages).

Nilsson, et al., "Elk1 and SRF transcription factors convey basal transcription and mediate glucose response via their binding sites in the human LXRB gene promoter" Nucleic Acids Research; Jul. 10, 2007; vol. 35, No. 14; pp. 4858-4868.

Jin, et al., "Increased SRF transcriptional activity in human and mouse skeletal muscle is a signature of insulin resistance" The Journal of Clinical Investigation; Mar. 2011; vol. 121, No. 3; pp. 918-929.

* cited by examiner

*Primary Examiner* — Jennifer McDonald
(74) *Attorney, Agent, or Firm* — Pierce Atwood LLP; Kevin M. Farrell; David J. Wilson

(57) ABSTRACT

Described are methods of improving glycemic control/improving insulin sensitivity by administering an inhibitor of Striated Muscle Activator of Rho Signaling (STARS) activity, and methods of identifying new compounds for use in the described methods of treatment.

6 Claims, 19 Drawing Sheets

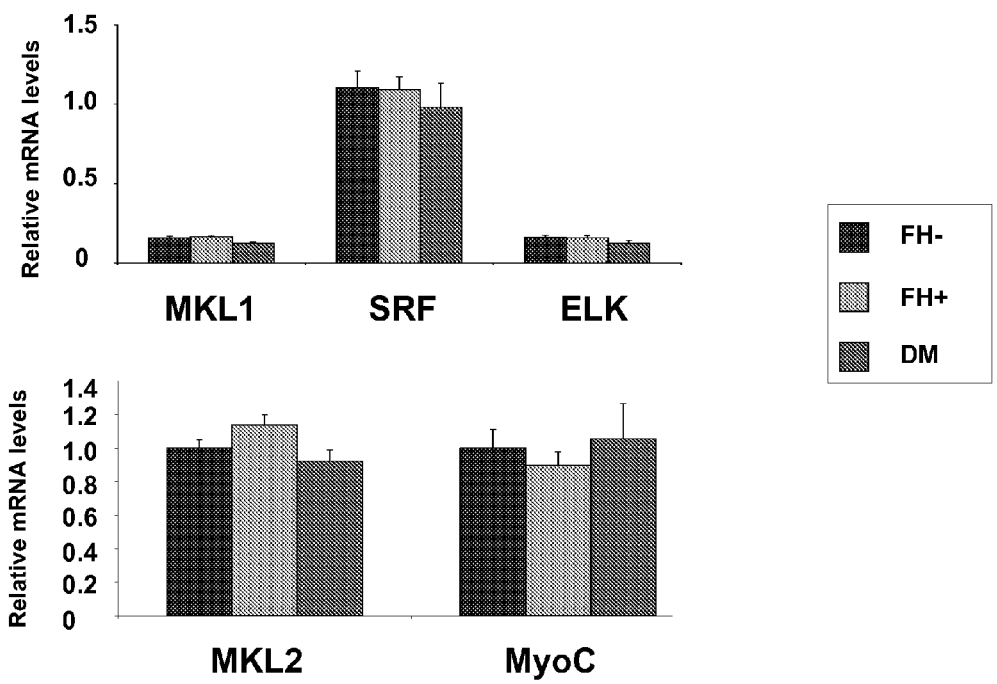
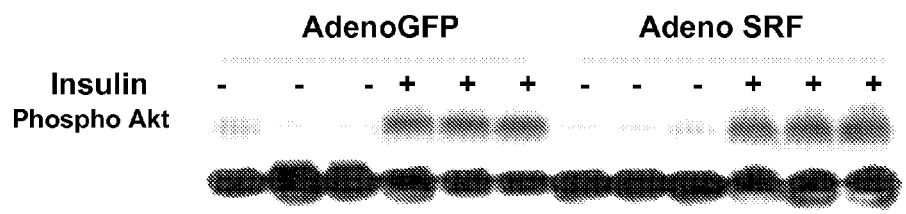

FIG. 14
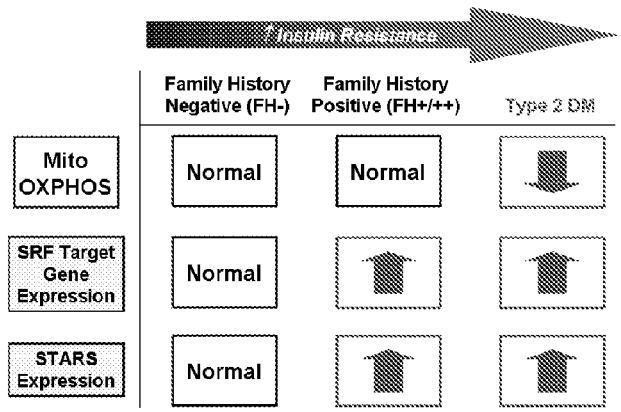
FIG. 15
A. Human Muscle Array Data
B. Human Muscle PCR
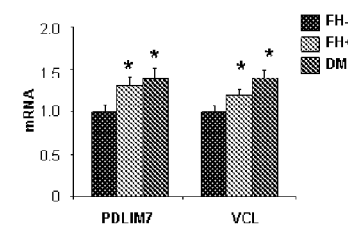
C. Mouse Muscle
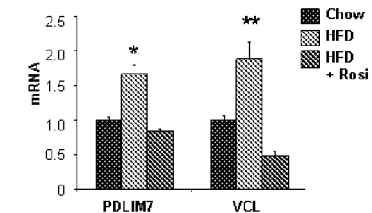

FIG. 21
A. Construct
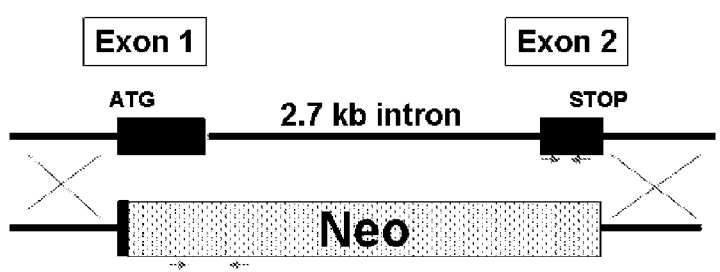
B. Genotyping
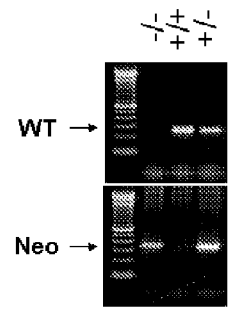
FIG. 22
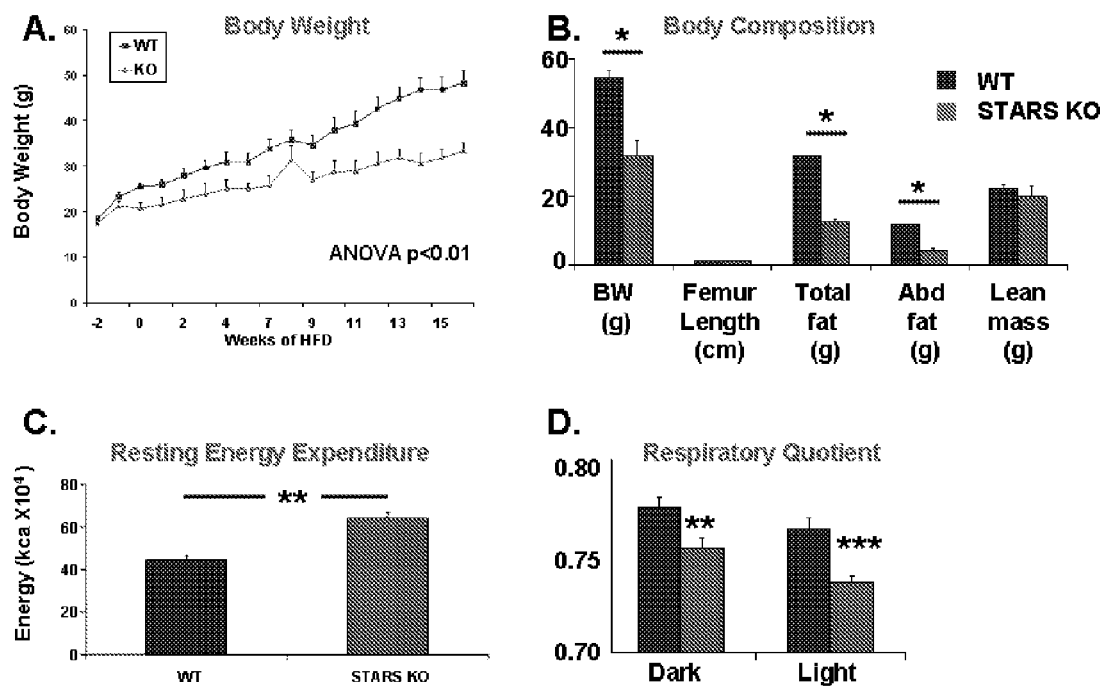

FIG. 23
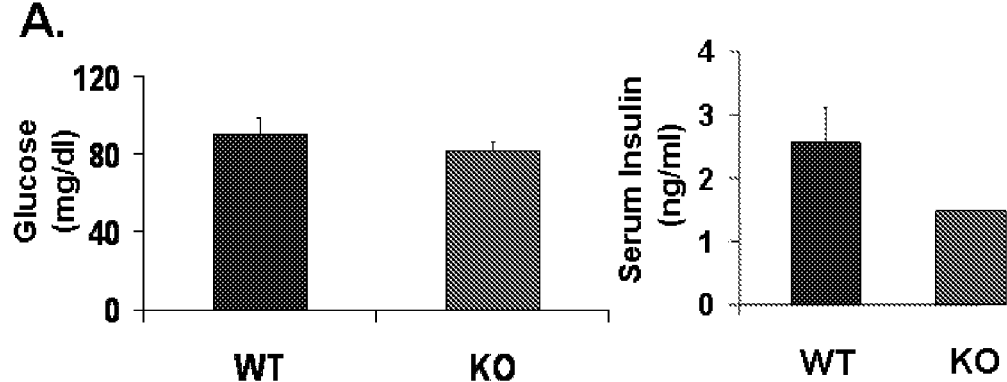
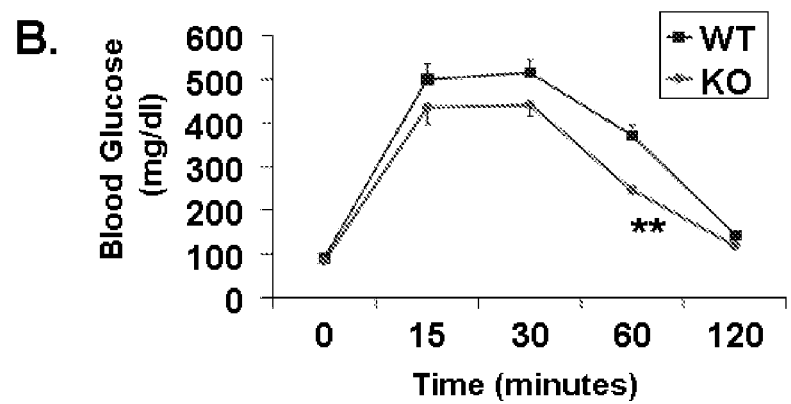

INHIBITING STRIATED MUSCLE ACTIVATOR OF RHO (STARS) TO IMPROVE GLYCEMIC CONTROL

FEDERALLY SPONSORED RESEARCH OR DEVELOPMENT

This invention was made with Government support under Grant No. DK62948 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 18, 2013, is named W2590174.txt and is 1,008 bytes in size.

TECHNICAL FIELD

This invention relates to methods of treating diabetes, e.g., to improving glycemic control, by administering one or more inhibitors of MLK1-dependent SRF transcriptional activity.

BACKGROUND

Cases of type 2 diabetes (DM2) are increasing at an alarming rate world wide, affecting up to 7% of the global population, making diabetes a major public health issue. Diabetes also exacts enormous personal tolls, among them long-term complications such as cardiovascular disease, retinopathy, neuropathy, and nephropathy. Worldwide, the incidence of diabetes is projected to continue to rise exponentially, reaching 366 million by 2030 (Wild et al., Diabetes Care 27:1047-1053 (2004)). There are many more undiagnosed diabetics and individuals who have insulin resistance or "pre-diabetes," and an unappreciated increased risk of developing diabetes. Thus, an important public health goal is to provide treatment strategies, and to implement prevention and early intervention strategies, including exercise, modest weight loss, and specific medication (Hu et al., N. Engl. J. Med. 345: 790-797 (2001); Tuomilehto et al., N. Engl. J. Med. 344:1343-1350 (2001)).

SUMMARY

The present invention is based, at least in part, on the discovery that expression of genes regulated by the transcription factor STARS (Striated Muscle Activator of Rho Signaling) is increased in humans with type 2 diabetes, and that inhibitors of STARS-mediated SRF transcriptional activity are useful in improving glycemic control. As discussed in the Exemplification section below, STARS mediates MLK1-dependent SRF transcriptional activity. In fact, it is the only known mediator of MLK1-dependent SRF transcriptional activity. Therefore, stated more generally, inhibitors of MLK1-dependent SRF transcriptional activity are useful in improving glycemic control. Reducing activation of SRF-dependent transcriptional pathways is a novel, directed approach that addresses the transcriptional dysregulation observed in humans with type 2 diabetes and at risk for type 2 diabetes.

In one aspect, the invention provides methods for improving glycemic control in a subject in need thereof. The methods include administering a therapeutically effective amount of an inhibitor of MLK1-dependent SRF transcriptional activity.

An example of such an inhibitor is an inhibitor of STARS-mediated transcriptional activity. In some embodiments, the inhibitor of MLK1-dependent SRF transcriptional activity, or STARS-mediated transcriptional activity is selected from the group consisting of small molecule inhibitors, dominant negatives, and inhibitory nucleic acids. In preferred embodiments the inhibitor specifically targets STARS.

In some embodiments, the subject has, or is at risk of developing, insulin resistance or type 2 diabetes mellitus.

In another aspect, the invention provides methods for identifying compounds useful in improving glycemic control. The methods include screening test compounds for the ability to inhibit MLK1-dependent SRF transcriptional activity generally, or STARS-mediated transcriptional activity specifically. Compounds that inhibit in these methods are candidate compounds for improving glycemic control, e.g., for treating insulin resistance or diabetes.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 6-7 are bar graphs showing that expression levels of SRF and its cofactors (MKL1, ELK, MKL2, MyoC (myocardin)) are not changed in insulin resistance and DM.

FIG. 8 is a phosphoimmunoblot showing phosphorylation of Akt in cells transfected with adenoviruses expressing either GFP (control) or SRF.

FIG. 14 is a schematic showing skeletal muscle expression patterns associated with insulin resistance and established type 2 DM. Expression of nuclear-encoded mitochondrial OXPHOS genes is reduced in humans with type 2 DM. Expression of SRF-dependent genes and the upstream regulator STARS are increased in both type 2 DM and insulin resistant subjects with diabetes family history.

FIG. 15A is a heat map of expression of individual SRF target genes progressively increased in both FH+ and DM2 (>1.2 fold in both comparisons vs. FH−). * indicates actin cytoskeleton-related gene.

FIGS. 15B and 15C are bar graphs depicting PCR expression analysis of SRF targets PDLIM7 and VCL in both (B) humans (FH−, FH+, DM2) and (C) C57BL/6 mice fed a high-fat diet (HFD, 60% calories from fat, 5 months). SRF target gene expression was normalized by rosiglitazone 3 mg/kg/day (n=7-9/group).

FIG. 21A is a schematic depicting the generation of STARS-null mice by homologous recombination.

FIG. 21B is an image of a PCR genotyping strategy.

FIG. 22A is a line graph showing that body weight is reduced in STARS-null mice (lower line) as compared with wild type controls fed high-fat diet (upper line).

FIG. 22B is a bar graph showing that STARS null mice have reduced adiposity on HFD, as assessed by DEXA.

FIGS. 22C and 22D are bar graphs showing increased energy expenditure and reduced respiratory quotient in STARS-null mice.

FIGS. 23A and 23B are graphs showing improved glucose homeostasis in STARS-null mice. FIG. 23A is a bar graph showing normal fasting glucose levels, but reduced fasting insulin levels in STARS-null mice. FIG. 23B is a line graph showing reduced glycemic excursion after IP glucose (2 g/kg glucose) ($p<0.05$ for AUC) with intraperitoneal glucose tolerance testing.

FIG. 24A is a bar graph showing that STARS-null mice ran >2 times longer than WT mice during treadmill testing, with parallel increase in total work and distance ($p<0.001$ for both). FIG. 24B is a line graph showing increased maximal oxygen consumption in STARS-null mice, with increased $VO_2$ max (7107±337 vs. 6077±115 ml/kg/hr, $p<0.05$).

DETAILED DESCRIPTION

Figure 1:
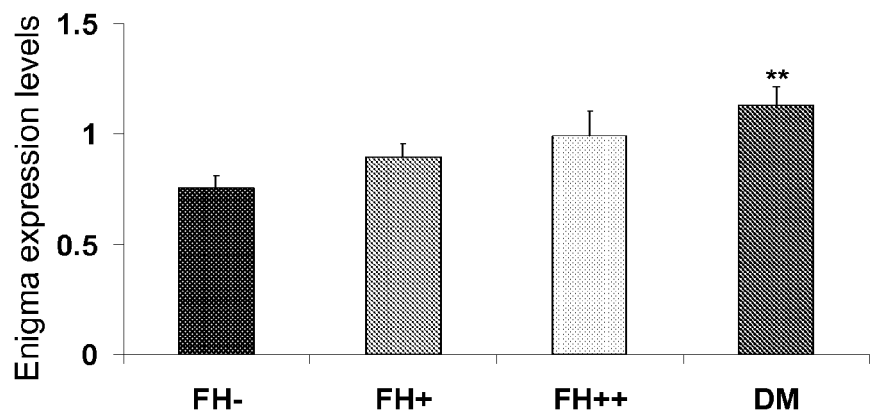
FIG. 1 is a bar graph showing that expression of enigma, an SRF target gene, is increased in muscle from humans with type 2 DM (T2DM). ** indicates $p<0.01$ by PCR.

To identify gene expression patterns potentially contributing to insulin resistance in this high-risk population, gene expression patterns were analyzed in muscle from metabolically characterized humans. The strongest signature in both FH+ and DM2 subjects is increased expression of actin cytoskeleton genes regulated by serum response factor (SRF) and its coactivator MKL1. G-actin, a negative co-regulator of SRF, was significantly decreased in muscle from an independent cohort of obese insulin resistant subjects. Similar patterns of enhanced SRF target expression and reduced G-actin were also observed in mice with dietary or genetic insulin resistance. Strikingly, modulation of MKL1 expression and/or reduced nuclear localization appears to be beneficial, as indicated by parallel expression modulation and chemical approaches. Firstly, siRNA-mediated reduction in MKL1 expression enhances both basal and insulin-stimulated glucose uptake in cultured myotubes. Secondly, the SRF transcriptional inhibitor CCG-1423 reduced nuclear translocation of MKL1 and in parallel, improved glucose uptake in cultured myotubes and improved in vivo glucose tolerance in mice made insulin resistant by high-fat feeding. Together, these findings demonstrate that upregulation of MKL1-dependent SRF transcriptional activity is an early signature of insulin resistance and genetic risk for type 2 diabetes.

As described herein, the present inventors have performed a cross-sectional human study to evaluate gene expression in muscle and abdominal adipose tissue biopsy from controls (family history negative in both parents and all first degree relative n=16), FH+ (offspring with one or two parent of diabetes n=25), and DM (n=11), to identify pathways affected early in diabetes that serve as markers for prevention and treatment of insulin resistance and DM, e.g., T2DM.

Selection of Subjects

Described herein are methods for the improvement of glycemic control, e.g., for the treatment or prevention of insulin resistance and/or T2DM. These methods are thus generally most suitable for those subjects who are in need of improved glycemic control. These subjects are generally insulin resistant and will often have, or be at risk of developing, T2DM. These subjects include those with one, two, or more risk factors for DM, e.g., obesity (BMI of 30 or above); age 45 or over; low birth weight (less than 3 kg); family history (first degree relative with a history of diabetes); low HDL cholesterol and high triglycerides; high blood pressure; personal history of gestational diabetes or gave birth to a baby weighing more than 9 pounds; minority group background (African American, American Indian, Hispanic American/Latino, or Asian American/Pacific Islander); and/or poor cardiorespiratory fitness as defined by an exercise test, e.g., a treadmill or cycle test (Sawada et al., Diabetes Care. 26:2918-2922 (2003)). In some embodiments, a subject suitable for treatment using a methods described herein is a subject with impaired glucose tolerance or impaired fasting glucose. In some embodiments, the subjects have the metabolic syndrome.

Non-Diabetic Subjects

In some embodiments, the subjects treated by the methods described herein do not have diabetes, i.e., are not diabetic. A person who is not diabetic has one or more of a Fasting Plasma Glucose Test result of 125 mg/dL or less; a 2-Hour Plasma Glucose Result in a Oral Glucose Tolerance Test of 199 mg/dL or less; and blood glucose level of less than 200 mg/dL. In these embodiments, the subjects treated by the methods described herein are not being treated for diabetes, e.g., have not been prescribed or are not taking insulin, meglitinides, biguanides, thiazolidinediones, or alpha-glucosidase inhibitors. In some embodiments the subjects are pre-diabetic, e.g., they have impaired glucose tolerance or impaired fasting glucose, e.g., as determined by standard clinical methods such as the intravenous glucose tolerance test (IVGTT) or oral glucose tolerance test (OGTT), e.g., a value of 7.8-11.0 mmol/L two hours after a 75 g glucose drink for impaired glucose tolerance, or a fasting glucose level (e.g., before breakfast) of 6.1-6.9 mmol/L.

The pathogenesis of type 2 diabetes is believed to generally involve two core defects: insulin resistance and β-cell failure (Martin et al., Lancet 340:925-929 (1992); Weyer et al., J. Clin. Invest. 104:787-794 (1999); DeFronzo et al., Diabetes Care. 15:318-368 (1992)). Important advances towards the understanding of the development of peripheral insulin resistance have been made in both animal models and humans (Bruning et al., Cell 88:561-572 (1997); Lauro et al., Nat. Genet. 20:294-298 (1998); Nandi et al., Physiol. Rev. 84:623-647 (2004); Sreekumar et al., Diabetes 51:1913-1920 (2002); McCarthy and Froguel, Am. J. Physiol. Endocrinol. Metab. 283:E217-E225 (2002); Mauvais-Jarvis and Kahn, Diabetes. Metab. 26:433-448 (2000); Petersen et al., N. Engl. J. Med. 350:664-671 (2004)). Thus, those subjects who have or are at risk for insulin resistance or impaired glucose tolerance are readily identifiable, and the treatment goals are well defined.

In some embodiments, the following charts can be used to select subjects who are not diabetic, but have pre-diabetes, i.e., impaired glucose tolerance and/or impaired fasting glucose.

TABLE 1

| Fasting Blood Glucose | |
|---|---|
| From 70 to 99 mg/dL (3.9 to 5.5 mmol/L) | Normal fasting glucose |
| From 100 to 125 mg/dL (5.6 to 6.9 mmol/L) | Impaired fasting glucose (pre-diabetes) |
| 126 mg/dL (7.0 mmol/L) and above on more than one testing occasion | Diabetes |
| Oral Glucose Tolerance Test (OGTT) [except pregnancy] (2 hours after a 75-gram glucose drink) | |
| Less than 140 mg/dL (7.8 mmol/L) | Normal glucose tolerance |
| From 140 to 200 mg/dL (7.8 to 11.1 mmol/L) | Impaired glucose tolerance (pre-diabetes) |
| Over 200 mg/dL (11.1 mmol/L) on more than one testing occasion | Diabetes |

Body Mass Index (BMI)

Obesity increases a subject's risk of developing T2D. BMI is determined by weight relative to height, and equals a person's weight in kilograms divided by height in meters squared (BMI=kg/m$^2$). Accepted interpretations are given in Table 2.

TABLE 2

| Category | BMI |
|---|---|
| Underweight | ≤18.5 |
| Normal weight | 18.5-24.9 |
| Overweight | 25-29.9 |
| Obese | ≥30 |

Thus, the methods described herein can include determining a subject's height, determining a subject's weight, and calculating BMI from the values determined thereby. Alternatively, the methods described herein can include reviewing a subject's medical history to determine their BMI.

In some embodiments, the methods described herein include selecting subjects who have a BMI of 30 or above (i.e., obese subjects).

Metabolic Syndrome

In some embodiments, the methods include determining whether a subject has the metabolic syndrome, and selecting the subject if they do have the metabolic syndrome, then administering a therapeutic compound as described herein. Determining whether a subject has the metabolic syndrome can include reviewing their medical history, or ordering or performing such tests as are necessary to establish a diagnosis.

The metabolic syndrome, initially termed Syndrome X (Reaven, Diabetes. 37(12):1595-1607 (1988)), refers to a clustering of obesity, dyslipidemia, hypertension, and insulin resistance. All components of the metabolic syndrome are traditional risk factors for vascular disease. As used herein, the metabolic syndrome is defined by the presence of at least 3 of the following: abdominal obesity (excessive fat tissue in and around the abdomen, as measured by waist circumference: e.g., greater than 40 inches for men, and greater than 35 inches for women), fasting blood triglycerides (e.g., greater than or equal to 150 mg/dL), low blood HDL (e.g., less than 40 mg/dL for men, and less than 50 mg/dL for women), high blood pressure (e.g., greater than or equal to 130/85 mmHg) and/or elevated fasting glucose (e.g., greater than or equal to 110 mg/dL). In some embodiments, levels of these criteria may be higher or lower, depending on the subject; for example, in subjects of Asian ancestry; see, e.g., Meigs, Curr. Op. Endocrin. Diabetes, 13(2):103-110 (2006). A determination of the presence of metabolic syndrome can be made, e.g., by reviewing the subject's medical history, or by reviewing test results.

Based on data from the Third National Health and Nutrition Examination Survey (NHANES III) approximately 24% of the adults in the United States qualify as having the metabolic syndrome (Ford et al., JAMA. 287(3):356-359 (2002)). Insulin resistance is now felt to be central in the pathogenesis of these related disorders.

Striated Activator of Rho Signaling (STARS)

STARS is an actin-binding protein that is expressed specifically in cardiac and skeletal muscle cells (Arai et al., J. Biol. Chem. 277(27):24453-9 (2002)). STARS binds to the I-band of the sarcomere and to actin filaments in transfected cells, where it activates Rho-signaling events. Arai et al. (2002), supra. STARS contains a unique, evolutionarily conserved domain that stimulates SRF-dependent transcription through a mechanism that requires actin polymerization, which is associated with increased skeletal muscle glucose uptake (Kanzaki, Endocrinology Journal, 53:267-293 (2006)), and Rho GTPase activation. STARS appears to activate SRF by inducing the nuclear translocation of myocardin-related transcription factors (MRTFs). STARS induces the nuclear accumulation of MRTF-A and -B and stimulates SRF-dependent transcription through a mechanism requiring Rho-actin signaling (Kuwahara et al., Mol. Cell. Biol. 25(8):3173-81 (2005). The sequence can be found, for example, in the Entrez Protein database maintained by the National Center for Biotechnology Information (NCBI) under the database accession number NP 631905 (amino acid).

STARS Interacting Proteins and Downstream Signaling Targets

A number of STARS-interacting proteins are known, including two novel members of the ABLIM protein family, ABLIM-2 and -3 (Barrientos et al., J. Biol. Chem. 282(11):8393-403 (2007)); and myocyte enhancer factor-2 (MEF2) (Kuwahara et al., J. Clin. Invest. 117(5):1324-34 (2007). As described herein, downstream signaling targets of STARS include RhoA (Arai et al., 2002, supra), and SRF. The sequence of human SRF is available at GenBank ID Nos. NM_003131.2 (nucleic acid) and NP_003122.1 (amino acid). See also, e.g., GeneID: 6722; Cooper et al., Genome Res. 17(2):136-44 (2007); and Zhang et al., Exp. Biol. Med. (Maywood) 233(3):297-309 (2008).

Inhibitory Nucleic Acids

The methods described herein can include targeting STARS. Methods of inhibiting proteins such as STARS are known in the art, and can include the use of small molecules, dominant negative, and inhibitory nucleic acids. For example, inhibitory nucleic acids, e.g., siRNA, antisense, ribozymes, or aptamers, directed against STARS can be used. siRNAs targeting STARS are known in the art (e.g., ABRA/STARS Stealth RNAi™ siRNA, Invitrogen) and are described herein.

RNA Interference

RNA interference (RNAi) is a process whereby double-stranded RNA (dsRNA) induces the sequence-specific regulation of gene expression in animal and plant cells and in bacteria (Aravin and Tuschl, FEBS Lett. 26:5830-5840 (2005); Herbert et al., Curr. Opin. Biotech. 19:500-505 (2008); Hutvagner and Zamore, Curr. Opin. Genet. Dev., 12:225-232 (2002); Sharp, Genes Dev., 15:485-490 (2001); Valencia-Sanchez et al. Genes Dev. 20:515-524 (2006)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), by microRNA (miRNA), functional small-hairpin RNA (shRNA), or other dsRNAs which are expressed in vivo using DNA templates with RNA polymerase II or III promoters (Zeng et al., Mol. Cell 9:1327-1333 (2002); Paddison et al., Genes Dev. 16:948-958 (2002); Denti, et al., Mol. Ther. 10:191-199 (2004); Lee et al., Nature Biotechnol. 20:500-505 (2002); Paul et al., Nature Biotechnol. 20:505-508 (2002); Rossi, Human Gene Ther. 19:313-317 (2008); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Scherer et al., Nucleic Acids Res. 35:2620-2628 (2007); Sui et al., Proc. Natl. Acad. Sci. USA 99(6):5515-5520 (2002).)

siRNA Molecules

In general, the methods described herein can use dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can be transcribed in vitro or in vivo, e.g., shRNA, from a DNA template. The dsRNA molecules can be designed using any method known in the art. Negative control siRNAs should not have significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The methods described herein can use both siRNA and modified siRNA derivatives, e.g., siRNAs modified to alter a property such as the specificity and/or pharmacokinetics of the composition, for example, to increase half-life in the body, e.g., crosslinked siRNAs. Thus, the invention includes methods of administering siRNA derivatives that include siRNA having two complementary strands of nucleic acid, such that the two strands are crosslinked. The oligonucleotide modifications include, but are not limited to, 2'-O-methyl, 2'-fluoro, 2'-O-methyoxyethyl and phosphorothioate, boranophosphate, 4'-thioribose. (Wilson and Keefe, Curr. Opin. Chem. Biol. 10:607-614 (2006); Prakash et al., J. Med. Chem. 48:4247-4253 (2005); Soutschek et al., Nature 432:173-178 (2004)).

In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The inhibitory nucleic acid compositions can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles). The inhibitory nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

siRNA Delivery

Direct delivery of siRNA in saline or other excipients can silence target genes in tissues, such as the eye, lung, and central nervous system (Bitko et al., Nat. Med. 11:50-55 (2005); Shen et al., Gene Ther. 13:225-234 (2006); Thakker, et al., Proc. Natl. Acad. Sci. U.S.A. (2004)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)).

Liposomes and nanoparticles can also be used to deliver siRNA into animals. Delivery methods using liposomes, e.g. stable nucleic acid-lipid particles (SNALPs), dioleoyl phosphatidylcholine (DOPC)-based delivery system, as well as lipoplexes, e.g. Lipofectamine 2000, TransIT-TKO, have been shown to effectively repress target mRNA (de Fougerolles, Human Gene Ther. 19:125-132 (2008); Landen et al., Cancer Res. 65:6910-6918 (2005); Luo et al., Mol. Pain 1:29 (2005); Zimmermann et al., Nature 441:111-114 (2006)). Conjugating siRNA to peptides, RNA aptamers, antibodies, or polymers, e.g. dynamic polyconjugates, cyclodextrin-based nanoparticles, atelocollagen, and chitosan, can improve siRNA stability and/or uptake. (Howard et al., Mol. Ther. 14:476-484 (2006); Hu-Lieskovan et al., Cancer Res. 65:8984-8992 (2005); Kumar, et al., Nature 448:39-43; McNamara et al., Nat. Biotechnol. 24:1005-1015 (2007); Rozema et al., Proc. Natl. Acad. Sci. U.S.A. 104:12982-12987 (2007); Song et al., Nat. Biotechnol. 23:709-717 (2005); Soutschek (2004), supra; Wolfrum et al., Nat. Biotechnol. 25:1149-1157 (2007))

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., Proc. Natl. Acad. Sci. USA 99(22):14236-40 (2002)).

Stable siRNA Expression

Synthetic siRNAs can be delivered into cells, e.g., by direct delivery, cationic liposome transfection, and electroporation. However, these exogenous siRNA typically only show short term persistence of the silencing effect (4~5 days). Several strategies for expressing siRNA duplexes within cells from recombinant DNA constructs allow longer-term target gene suppression in cells, including mammalian Pol II and III promoter systems (e.g., H1, U1, or U6/snRNA promoter systems (Denti et al. (2004), supra; Tuschl (2002), supra); capable of expressing functional double-stranded siRNAs (Bagella et al., J. Cell. Physiol. 177:206-213 (1998); Lee et al. (2002), supra; Miyagishi et al. (2002), supra; Paul et al. (2002), supra; Scherer et al. (2007), supra; Yu et al. (2002), supra; Sui et al. (2002), supra).

Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

In another embodiment, siRNAs can be expressed in a miRNA backbone which can be transcribed by either RNA Pol II or III. MicroRNAs are endogenous noncoding RNAs of approximately 22 nucleotides in animals and plants that can post-transcriptionally regulate gene expression (Bartel, Cell 116:281-297 (2004); Valencia-Sanchez et al., Genes & Dev. 20:515-524 (2006)). One common feature of miRNAs is that they are excised from an approximately 70 nucleotide precursor RNA stem loop by Dicer, an RNase III enzyme, or a homolog thereof By substituting the stem sequences of the miRNA precursor with the sequence complementary to the target mRNA, a vector construct can be designed to produce siRNAs to initiate RNAi against specific mRNA targets in mammalian cells. When expressed by DNA vectors containing polymerase II or III promoters, miRNA designed hairpins can silence gene expression (McManus (2002), supra; Zeng (2002), supra).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage, destabilization, and/or translation inhibition destruction. In this fashion, the mRNA to be targeted by the siRNA generated from the engineered RNA precursor will be depleted from the cell or organism, leading to a decrease in the concentration of the protein encoded by that mRNA in the cell or organism.

Antisense

An "antisense" nucleic acid can include a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof (for example, the coding region of a target gene). In another embodiment, the antisense nucleic acid molecule is antisense to a "noncoding region" of the coding strand of a nucleotide sequence encoding the selected target gene (e.g., the 5' and 3' untranslated regions).

An antisense nucleic acid can be designed such that it is complementary to the entire coding region of a target mRNA but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

The antisense nucleic acid molecules of the invention are typically administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense nucleic acid molecule of the invention is an ∀-anomeric nucleic acid molecule. An ∀-anomeric nucleic acid molecule forms specific double-stranded hybrids with complementary RNA in which, contrary to the usual θ-units, the strands run parallel to each other (Gaultier et al., Nucleic Acids. Res. 15:6625-6641 (1987)). The antisense nucleic acid molecule can also comprise a 2'-O-methylribonucleotide (Inoue et al. Nucleic Acids Res. 15:6131-6148 (1987)), a 2'-O-methoxyethylribonucleotide, a locked nucleic acid, an ethylene-bridged nucleic acid, an oxetane-modified ribose, a peptide nucleic acid, or a chimeric RNA-DNA analogue (Inoue et al. FEBS Lett., 215: 327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region, e.g., promoters and/or enhancers) to form triple helical structures that prevent transcription of the target gene in target cells. See generally, Helene, C. Anticancer Drug Des. 6:569-84 (1991); Helene, C. Ann. N.Y. Acad. Sci. 660:27-36 (1992); and Maher, Bioassays. 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Additional information regarding antisense technologies and their use in vivo can be found in Crooke, *Antisense Drug Technology: Principles, Strategies, and Applications*, (CRC Press, 2007)

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target-protein encoding nucleic acid can include one or more sequences complementary to the nucleotide sequence of a target cDNA disclosed herein, and a sequence having known catalytic sequence responsible for mRNA cleavage (see U.S. Pat. No. 5,093,246 or Haselhoff and Gerlach, Nature. 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science. 261: 1411-1418 (1993).

Pharmaceutical Compositions

The methods described herein include the manufacture and use of pharmaceutical compositions, which include compounds identified by a method described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol. 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of Treatment

The methods described herein include methods for the treatment of disorders associated with impaired glucose tolerance, e.g., for the improvement of glycemic control and insulin sensitivity. In some embodiments, the disorder is type 2 diabetes. Generally, the methods include administering a therapeutically effective amount of therapeutic compound as described herein, to a subject who is in need of, or who has been determined to be in need of, such treatment.

As used in this context, to "treat" means to ameliorate at least one symptom of the disorder associated with impaired glucose tolerance. Often, impaired glucose tolerance results in hyperglycemia; thus, a treatment can result in a return or approach to normoglycemia/normal insulin sensitivity. As used in this context, to "prevent type 2 DM" means to reduce the likelihood that a subject will develop type 2 DM. One of skill in the art will appreciate that a preventive treatment is not required to be 100% effective, but can instead result in a delay in the onset of T2DM, or a reduction in symptoms, e.g., an improvement in glucose tolerance.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Methods of Screening

The invention includes methods for screening of test compounds, to identify compounds that modulate a pathway described herein, e.g., compounds that (i) reduce the expression or activation of STARS, thereby reducing SRF activity, (ii) reduce the binding of STARS to actin; or (iii) affect MRTF localization, e.g., reduce nuclear localization and/or increase cytoplasmic localization, thereby reducing STARS and/or SRF activity, and enhancing oxygen consumption, glucose uptake, and/or insulin sensitivity.

The methods described herein can be used to identify compounds that bind to STARS. In addition, the effect of a test compound on STARS-mediated SRF-induced transcription activity can be determined For example, the methods can be used to identify compounds that demonstrate binding to STARS, and decrease STARS-induced transcription of a STARS-regulated gene.

Thus, in general, the methods will include providing a sample that includes STARS.

Screening methods suitable for use in these embodiments are known in the art and include, but are not limited to, yeast or mammalian 2-hybrid systems, tagged protein assays, immunoprecipitation assays, and proteomics assays. These methods can be used to identify natural (i.e., endogenous) regulators of STARS, for example.

In order to evaluate the ability of a compound to affect STARS activity, it will generally be desirable to test the compound in a cell. For example, the methods can include adding the compound to cells that have a functional serum-induced signaling pathway. The methods can then include contacting the cells with the compound, and evaluating an effect of the compound on STARS activity or on SRF activity (e.g., expression of a SRF-induced gene such as enigma, ZYX, VCL, and/or PDLIM7), e.g., using methods known in the art for monitoring gene expression, e.g., using a reporter construct including a detectable reporter gene (such as a fluorescent protein) operably linked to a SRF-response element, e.g., from the noncoding sequence of enigma, ZYX, VCL, and/or PDLIM7 (see the Examples below, describing the use of SRF binding element (SRE) CArG boxes (Kuwahara et al., Mol. Cell Biol. 25:3173-3181 (2005)) promoter in a reporter construct).

The ability of a test compound to affect subcellular localization of MRTF-A and/or MRTF-B can be assayed, using methods known in the art, e.g., expression of fluorescently labeled MRTF-A and/or MRTF-B. Compounds that promote cytoplasmic rather than nuclear localization of MRTF-A and/or MRTF-B, or that inhibit expression or activity of MRTF-A and/or MRTF-B, would also be useful in the treatment of insulin resistance or diabetes.

Test Compounds

The test compounds can be, e.g., natural products or members of a combinatorial chemistry library.

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library. These methods can also be used, for example, to screen a library of proteins or fragments thereof, e.g., proteins that are expressed in liver or pancreatic cells.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules, e.g., as exemplified by Obrecht and Villalgordo, *Solid-Supported Combinatorial and Parallel Synthesis of Small-Molecular-Weight Compound Libraries*, Pergamon-Elsevier Science Limited (1998). Such methods include the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, θ-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides.

In some embodiments, test compounds and libraries thereof can be obtained by systematically altering the structure of a first test compound. Taking a small molecule as an example, e.g., a first small molecule is selected that is, e.g., structurally similar to a known phosphorylation or protein recognition site. For example, in one embodiment, a general library of small molecules is screened, e.g., using the methods described herein, to select a first test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" (e.g., test compounds that demonstrate activity in a method described herein) in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in treating disorders described herein. Thus, the invention also includes compounds identified as "hits" by a method described herein, and methods for their administration and use in the treatment, prevention, or delay of development or progression of a disease described herein.

EXAMPLES

The invention is further described in the following examples, which do not limit the scope of the invention described in the claims.

Example 1

Increased SRF Pathway Activity in Humans with Insulin Resistance

To identify the earliest genes that can cause DM2, whole genome DNA microarrays were performed in muscle and adipose biopsies from 53 human subjects which included non-diabetic subjects, those without diabetes family history in any first-degree relative, identified herein as "FH−" (n=15), those with one or two parents with type 2 diabetes ("FH+," n=26), and those with established type 2 diabetes ("DM," n=11).

All subjects underwent a 75 mg oral glucose tolerance test. Adipose and muscle biopsies were taken before and after hyperinsulinemic-euglycemic clamp. Insulin sensitivity index (Si) was estimated by glucose disposal rate and insulin secretion based on intravenous glucose tolerance tests, all of which were performed using standard clinical methodology.

Consistent with a previous study (Martin et al., Lancet. 340:925-929 (1992); Patti et al., Proc. Natl. Acad. Sci. USA. 100:8466-8471 (2003)), the results confirmed that the FH+ group had normal HgbA1c and fasting glucose levels. However, fasting insulin levels were significantly increased compared to the FH− group. Furthermore, the insulin sensitivity index (Si), a measure of the ability of insulin to regulate glucose uptake and metabolism, was significantly reduced (by about half of normoglycemic FH− subject group) in the FH+ group, and was further decreased to one third of normal in the DM group (see Table 3), which indicates that FH+ subjects were insulin resistant.

TABLE 3

|  | FH− | FH+ | DM |
| --- | --- | --- | --- |
| Gender | 7M/8F | 11M/15F | 4M/7F |
| Age | 37.8 ± 2.9 | 37.7 ± 2.1 | 51.5 ± 3.6** |
| BMI (kg/m$^2$) | 25.2 ± 0.8 | 28.1 ± 1.2 | 30.8 ± 2.5* |
| Hemoglobin A1c (Normal 4-6%) | 5.0 ± 0.1 | 5.1 ± 0.1 | 6.8 ± 0.4*** |
| Fasting glucose (mg/dL) | 89.9 ± 5.8 | 92.6 ± 1.5 | 127.0 ± 14.4** |
| Fasting insulin (μU/mL) | 5.8 ± 0.8 | 8.7 ± 1.1# | 21.5 ± 7.1* |

TABLE 3-continued

|  | FH− | FH+ | DM |
|---|---|---|---|
| Si (Insulin Sensitivity) | 7.0 ± 0.9 | 4.1 ± 0.5# | 2.4 ± 0.5*** |
| M (high) mg/kg/min | 8.6 ± 0.5 | 6.8 ± 0.4# | ND |

Human Clinical data showed that various parameters related to type 2 diabetes are significantly altered according to disease progress e.g. FH+ insulin resistant group to DM group.
*Indicate P < 0.05;
**Indicate P < 0.001;
***Indicate P < 0.001 comparison between DM vs FH−.
Indicate P < 0.05 comparison between FH+ vs FH−.
Abbreviation:
FH−, without Family history of diabetes;
FH+, one or two parents with diabetes;
DM, type 2 diabetes.

In order to discover specific pathways that might contribute to the pathogenesis of DM2, we initially performed gene set enrichment analysis using the GSEA program (available on the world wide web at broad.mit.edu/gsea/), which defines differences in sets of genes between groups (Mootha et al., Nat. Genet. 34:267-273 (2003)) to identify the most significantly altered gene pathways. Interestingly, two pathways stood out. The results demonstrated that serum inducible megakaryoblastic leukemia (translocation) 1 (MKL1) dependent and independent serum response factor (SRF) target genes (Selvaraj and Prywes, BMC. Mol Biol. 5:13 (2004)) and cytoskeleton pathways were the top ranking gene sets significantly enriched in FH+ insulin resistance and DM2 groups, both in muscle and adipose tissues.

Additional pathway analysis using MAPPFinder confirmed that serum response factor (SRF)-dependent and actin-related cytoskeleton gene expression is increased in diabetes, and more importantly, also in insulin resistance. The top-ranking single gene differentially expressed in skeletal muscle in the fasting state is the Actin-binding Rho activating protein (ABRA), or STARS, increased by 2.5 fold in individuals with type 2 diabetes (p<0.01). This gene regulates intracellular actin dynamics and subcellular localization of MKL1/2, thus contributing to SRF-dependent gene transcription. Since disruption of actin by latrunculin B increases STARS expression in C2C12 cells by 50% in C2C12 myotubes (p<0.03, not shown), it was hypothesize that increased STARS expression in DM may reflect disruption of actin dynamics and also contribute to the pattern of increased SRF-related gene expression. Similar patterns of SRF-dependent expression are also observed in adipose tissue from insulin resistant subjects and in insulin resistant muscle.

Alterations in genes related to the actin cytoskeleton are also a feature of both insulin resistance and DM. For example, enigma (FIG. 1) is an APS binding partner that colocalizes with both actin and the insulin receptor. Indeed, previous studies have shown that overexpression of enigma reduces GLUT4 translocation and glucose uptake.

Example 2

Increases in SRF-Related Actin Cytoskeleton Genes in Insulin Resistant Subjects

Figure 2:
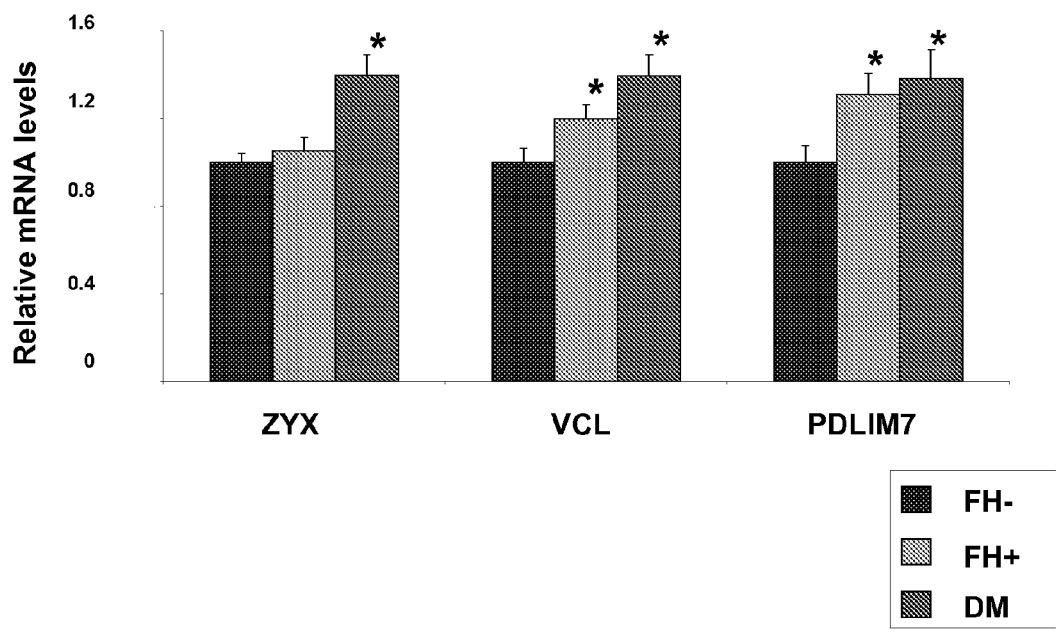
FIG. 2 is a bar graph showing that expression levels of a subset of SRF target genes is increased in humans with insulin resistance and DM2, as determined by quantitative RT-PCR. ZYX, zyxin; VCL, vinculin; PDLIM7, PDZ and LIM domain 7; FH−, subjects without a diabetes family history in any first-degree relative, dark grey; FH+, subjects with one or two parents with type 2 diabetes, light grey; DM, subjects with established type 2 diabetes, medium grey.

SRF is a transcription factor that induces expression of many types of genes including muscle and growth associated genes, and plays a predominant role in inducing expression of actin cytoskeletal genes (Sotiropoulos et al., Cell. 98:159-169 (1999)). SRF was previously shown to be a master regulator of the actin cytoskeleton (Posern and Treisman, Trends Cell Biol. 16:588-596 (2006)). Multiple lines of evidence indicate that the actin cytoskeleton has an important role in glucose uptake (Brozinick et al., J. Biol. Chem. 279:40699-40706 (2004); Barres et al., Mol. Endocrinol. 20:2864-2875 (2006)). In addition to many SRF-regulated genes that are categorized as transcriptional factor and immediately early genes, many of these genes are also related to actin cytoskeleton. To confirm this, quantitative real time polymerase chain reaction (qRT-PCR) was performed in human muscle tissue biopsies. Consistent with DNA microarray results, several actin cytoskeletal genes including MKL1 dependent SRF target genes; vinculin (VCL), zyxin (ZYX) and MKL1 independent target gene; PDZ and LIM domain 7 (PDLIM7, also known as enigma) (see Schratt et al., Mol. Cell. Biol. 21(8): 2933-43 (2001)) were significantly increased in both FH+ and DM (FIG. 2).

Figure 3A:
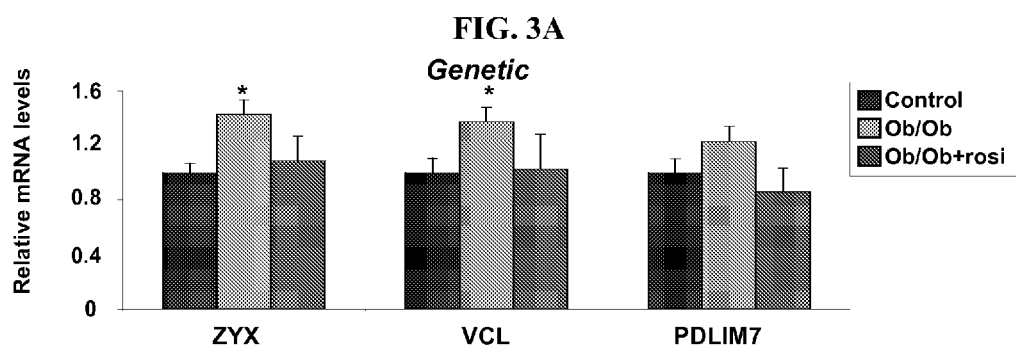
FIGS. 3A-B are bar graphs showing that expression of SRF target genes is also increased in mice with insulin resistance due to a genetic predisposition (Ob/Ob, 3A) or diet (high fat chow, HFC, 3B), and this increase is normalized by rosiglitazone. ARPC2, actin related protein 2/3 complex, subunit 2, 34 kDa.
Figure 3B:
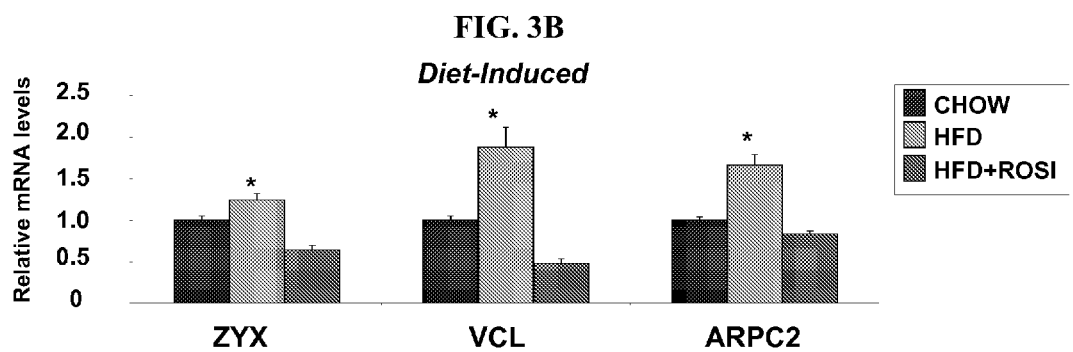
Figure 4:
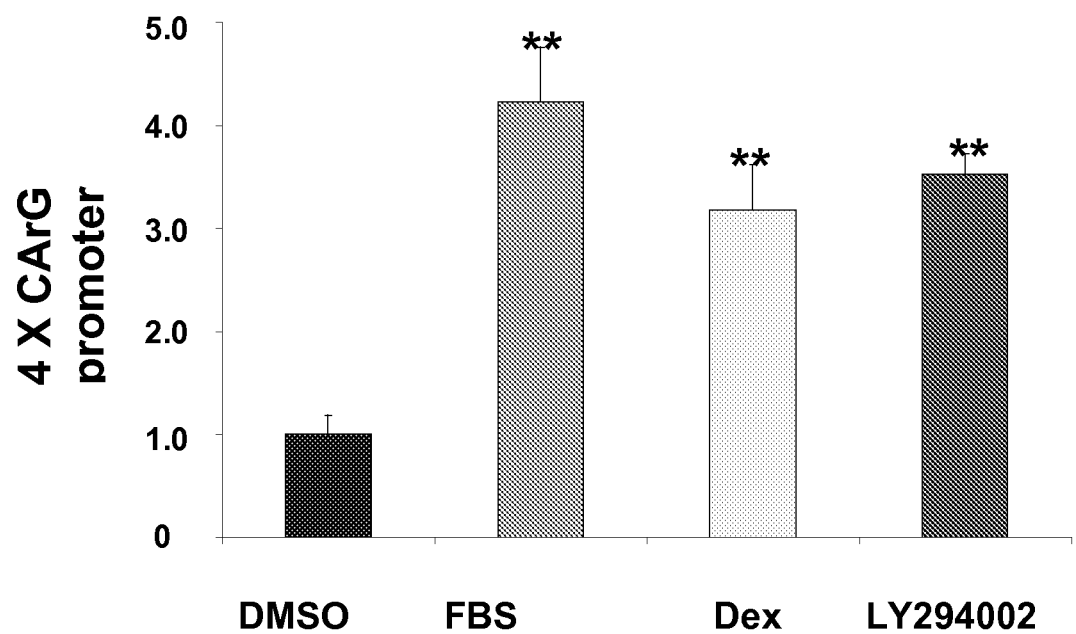
FIG. 4 is a bar graph showing that SRF transcriptional activity is increased in experimental insulin resistance. Dex, dexamethasone; FBS, fetal bovine serum (control); DMSO, dimethyl sulfoxide (control/vehicle)
Figure 5A:
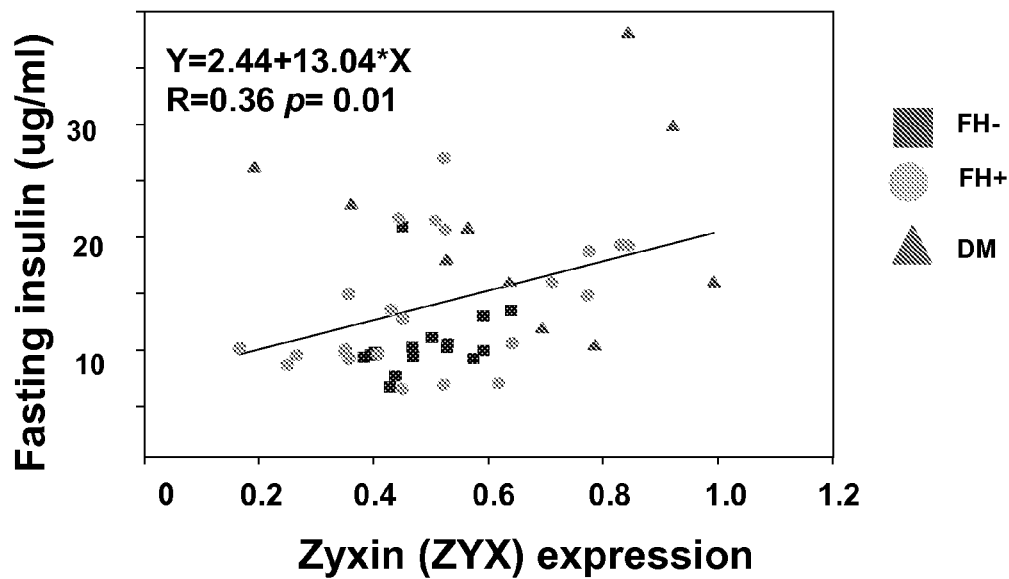
FIGS. 5A-B are scatter/line graphs showing that SRF-dependent target gene expression correlated with metabolic phenotypes; the graphs illustrate the relationship between fasting insulin levels and zyxin expression (5A) or fasting glucose and vinculin expression (5B).
Figure 5B:
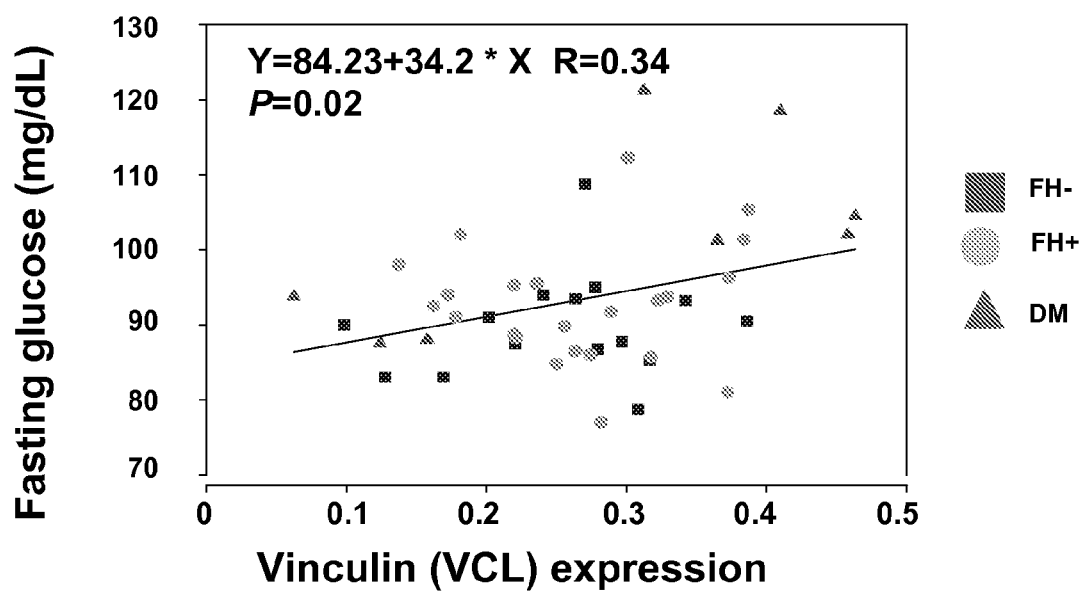

To determine whether increased SRF related actin cytoskeletal gene expression might be a consequence of insulin resistance, two different type of insulin resistance mouse models were used, the diet induced obesity (DIO) mice and genetically obese (Ob/Ob) mice. Consistent with the above human tissue gene expression results, increased expression of ZYX, VCL and PDLIM7 was observed in muscles from both DIO and Ob/Ob mice. Expression levels were normalized by rosiglitazone (an insulin sensitizing agent), see FIGS. 3A-B. Similar results were also observed in several experimentally-induced insulin resistance cell models, including dexamethasone- and LY294002-induced insulin resistance (cells were treated overnight with 10 µM of the induction agent), as shown in FIG. 4. Furthermore, there was significant enrichment of MKL1-dependent and -independent SRF pathways in FFA-palmitate treated C2C12 myotubes as compared with control BSA treated cells. Interestingly, there was a significant correlation of these genes with human metabolic phenotypes, e.g., zyxin and fasting insulin (p=0.01), vinculin and fasting glucose (p=0.02) (FIGS. 5A-B). These results strongly suggest that up-regulation of SRF related actin cytoskeleton are an early signature of insulin resistance and may influence insulin sensitivity.

Example 3

Elevated ELK1 and SRF Transcriptional Activity in Insulin Resistance

In light of the experiments described above, levels of expression of SRF and it co-factors were evaluated in insulin resistance. Surprisingly, the expression of SRF and its well known co-activators; including ETS domain-containing protein Elk-1 (ELK1) and megakaryoblastic leukemia (translocation) 1 (MKL1) did not show any changes either in human tissue biopsy from FH+ and DM or insulin resistant mouse skeletal muscle tissues (FIGS. 6-7). Despite unchanged expression levels of SRF and its cofactors, up-regulation of SRF target genes raised several possibilities, e.g., that (i) changes of DNA binding activity of SRF and its cofactors to the target gene promoter may increase expression of SRF target genes in insulin resistance, (ii) SRF transcriptional activity may be up-regulated in insulin resistant and DM state, or (iii) localization of co-regulator might be changed in insulin resistance.

To explore the above possibility, DNA binding activity of SRF and it co-factor ELK1 to the target gene promoter was first evaluated. To this end, electrophoretic mobility shift assays (EMSA) were performed. The results indicated that SRF and ELK1 DNA binding activity to the SRF binding element (SRE) were increased in myotubes from insulin resistant patients as compared to normal healthy subjects. These results suggest that in the insulin resistant state, SRF target gene expression might be mediated by increased SRF and ELK1 DNA binding to the promoter region of target genes. In support of this idea, in low density DNA binding arrays, SRF DNA binding activity was increased in primary myotubes from insulin resistant human and free fatty acid (FFA)-treated C2C12 myotubes compared to control (5-10 fold, respectively).

To determine whether SRF transcriptional activity is also changed in insulin resistance, 4× tandem repeat of SRF binding element (SRE) CArG boxes (Kuwahara et al., Mol. Cell Biol. 25:3173-3181 (2005)) promoters linked to a luciferase gene were used as a reporter. In C2C12 myotubes, SRF transcriptional activity was dramatically increased in multiple experimentally induced insulin resistance (e.g., dexamethasone, PI3 kinase inhibitor-LY294002, FFA) at basal level (FIG. 4). These increases in SRF transcriptional activity in insulin resistant states could cause up-regulation of SRF target gene expression.

Example 4

G Actin, a Negative Co-Regulator of SRF, is Decreased in Insulin Resistance

G actin is not only a component of the cytoskeleton but also acts as a signalling regulator to modulate gene expression together with SRF cofactor MKL1 (Vartiainen et al., Science. 316:1749-1752 (2007)). In the nucleus, MKL1 forms a complex with G actin, and it is active on target gene promoters only after dissociating from G actin. The amount of nuclear G actin sufficient to block SRF transcriptional activity has been shown (Miralles, Cell 113, 329-342 (2003); Sotiropoulos et al., Cell 98, 159-169 (1999)}. Thus, changes in the amount of G actin might account for up-regulation of SRF target gene expression. To address this point, rectus muscles from lean and obese and/or impaired glucose tolerance (IGT) human subjects were stained with rhodamine-conjugated DNase I, a marker of G actin, and FITC-conjugated phalloidin, a marker of F actin. Surprisingly, DNase stainable muscle G actin was dramatically reduced in obese and/or IGT human muscle compare to normal lean subject. Moreover, G actin was predominantly colocalized with the nuclear stain DAPI, indicating that nuclear G actin likely plays an important role in progression of disease.

This phenomenon is further confirmed in diet induced obesity (DIO) mice, which showed dramatic decreases in G actin staining as compared to control mice; this decrease is partially normalized by treatment with the insulin sensitizer rosiglitazone. Consistently, similar results were seen in C2C12 myotubes: the amount of DNase I stainable G actin was decreased in either dexamethasone or LY treated cells, and was partially recovered by rosiglitazone treatment. These results suggest that decreases in DNase I stainable G actin levels are responsible for increases in SRF transcriptional activity in insulin resistant states.

Since MKL1 is known to shuttle between the cytosol and nucleus to modulate target gene expression (Vartiainen et al., Science. 316:1749-1752 (2007)), the possibility arises that MKL1 localization may differ in insulin resistant state as compared to the normal state. To demonstrate this cellular localization of MKL1 was examined in C2C12 myoblast. In the basal state, MKL1 predominantly localized to cytosol and partially in nucleus. After 30 minutes of serum stimulation, MKL1 translocated to the plasma membrane. However, when the cells were treated with dexamethasone or LY294002, MKL1 was retained in the nucleus. To determine whether MKL1 and G actin complex formation is changed in insulin resistance, the nuclear and cytosolic fractions from C2C12 myotubes were co-immunoprecipitated with MKL1 and blotted with beta actin. The results revealed that the nuclear proportion of G actin was dramatically decreased in dexamethasone-induced insulin resistant state as compared to serum stimulated state. Thus, these data indicate that, in the insulin resistant state, nuclear MKL1 forms complexes with G actin and this is sufficient to induce target gene expression.

siRNA was used to specifically reduce MKL1 expression, achieving an effective knockdown of about 60%. This increased insulin-stimulated phosphorylation of Akt (Ser473), expressed relative to total Akt protein content, by 2-fold ($p<0.01$). Moreover, this reduction in MKL1 expression enhanced basal glucose uptake in cultured myotubes by 1.9-fold ($p<0.03$); similar trends were observed for increases in insulin-stimulated glucose uptake (43% higher, $p=0.13$ for single experiment). Thus, siRNA-mediated reduction in MKL1 expression enhances both basal and insulin-stimulated glucose uptake in cultured myotubes.

Example 5

Inhibiting SRF Transcriptional Activity Improves Insulin Sensitivity

Taken together, the above results together suggest that modulating SRF expression and/or transcriptional activity might change insulin sensitivity. To address this question, two distinct approaches were used: (i) modulation of expression of SRF by adenoviral over-expression of SRF and siRNA knockdown SRF, and (ii) administration of a specific inhibitor for SRF transcriptional activity.

Figure 9:
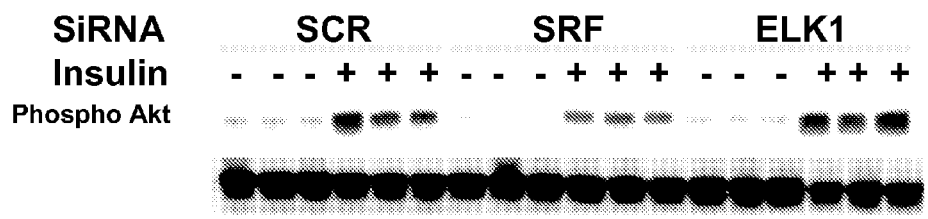
FIG. 9 is a phosphoimmunoblot showing phosphorylation of Akt in cells expressing siRNA directed against SRF, or ELK1. A scrambled siRNA (SCR) was included as a control.
Figure 10:
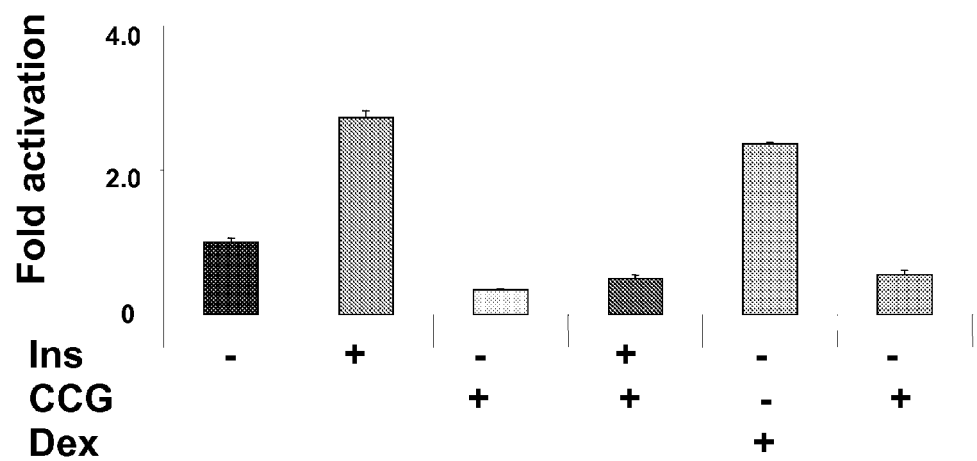
FIG. 10 is a bar graph showing that CCG-1423 inhibits SRF activity in C2C12 myotubes, reversing dexamethasone-induced decreases in SRF activity.
Figure 11A:
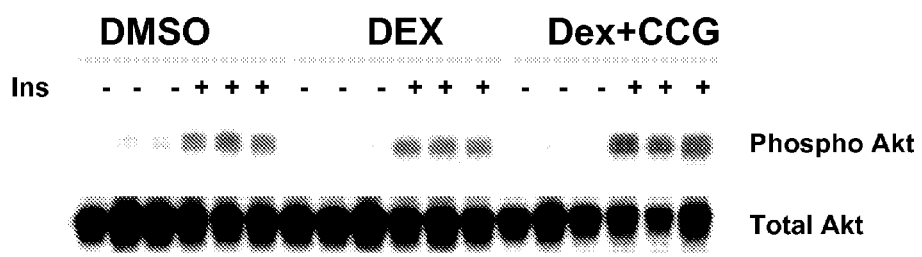
FIG. 11A is a phosphoimmunoblot showing phosphorylation of Akt in cells treated with dexamethasone alone or in combination with CCG-1423. DMSO treated cells served as a control. The results show that CCG-1423 improves insulin-stimulated Akt phosphorylation.

The adenoviral overexpression of SRF did not have an effect on Akt phosphorylation (a marker of insulin sensitivity), either in basal or insulin stimulated state (FIG. 8). Unexpectedly, knockdown of SRF by siRNA in C2C12 myotubes showed decreased Akt phosphorylation (FIG. 9). These results indicate that modulation of SRF expression has less impact on insulin sensitivity. Surprisingly, knockdown of ELK1 expression in myotubes increased Akt phosphorylation upon insulin stimulation, although there was no significant difference in the unstimulated state. These data support the importance of SRF cofactors including ELK1 in the regulation of SRF target gene expression The next experiments were performed to determine whether SRF transcriptional activity, rather than expression of SRF itself, is important for maintaining appropriate insulin sensitivity. A new compound, CCG-1423, is available for specifically inhibiting SRF transcriptional activity (Evelyn et al., Mol. Cancer Ther. 6:2249-2260 (2007)). First, it was confirmed that this compound specifically blocks SRF transcriptional activity induced by serum, dexamethasone, and insulin (FIG. 10). CCG-1423 was then evaluated to test the possibility that reducing SRF transcriptional activity improves insulin sensitivity. Indeed, this is the case. A dramatic improvement in insulin sensitivity resulted from treatment with CCG-1423 in dexamethasone-induced insulin resistant myotubes, as CCG-1423 increased insulin-simulated Akt phosphorylation (a marker of insulin sensitivity) (FIG. 11A).

Figure 11B:
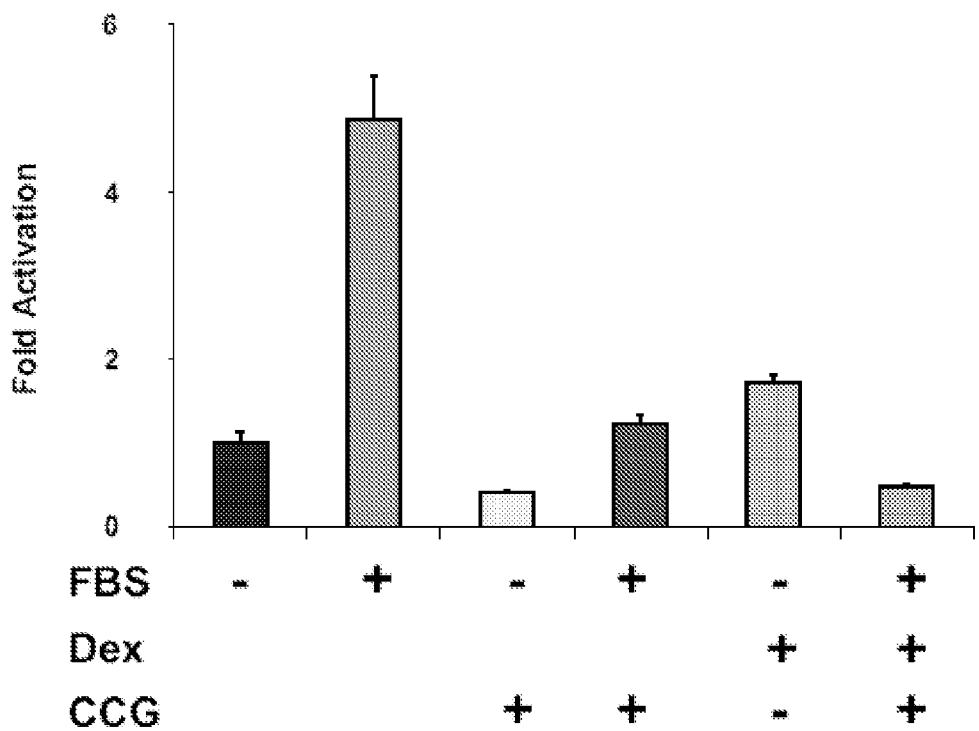
FIG. 11B is a bar graph showing the effect of CCG on SRF transcriptional activity. 4× CArG promoter is activated in response to serum stimulation (FBS 2 hours, control) and following overnight treatment with 100 μM dexamethasone (DEX) in C2C12 myoblasts. This SRF-mediated transcriptional activity was blocked by pre-treatment with CCG-1423 (1 μM, 16 hours).

CCG-1423 reduced SRE promoter activity and efficiently blocked both serum- and dexamethasone-stimulated activation (FIG. 11B). To determine if the effects of CCG-1423 on SRF activity were mediated via MKL1 localization, MKL1 localization was assessed in C2C12 myoblasts treated with CCG-1423. MKL1 was predominantly nuclear following treatment with dexamethasone. By contrast, MKL1 was almost exclusively localized to the cytoplasm in cells treated with CCG-1423; more importantly, CCG-1423 reversed dexamethasone-induced MKL1 nuclear localization to partial cytoplasmic localization. Thus, these data indicate that CCG-1423 represses SRF activity, at least in part by regulation of MKL1 cytosol/nuclear localization.

Figure 11C:
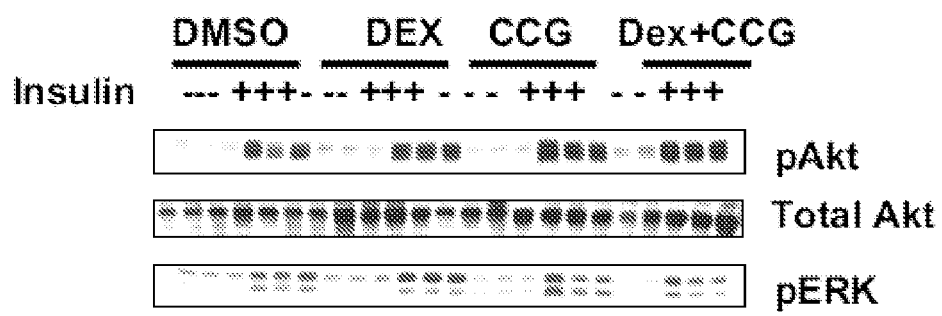
FIG. 11C is a phosphoimmunoblot showing that CCG-1423 increases insulin-stimulated Akt phosphorylation (100 nM, 10 minutes), with minimal change in ERK phosphorylation.
Figure 11D:
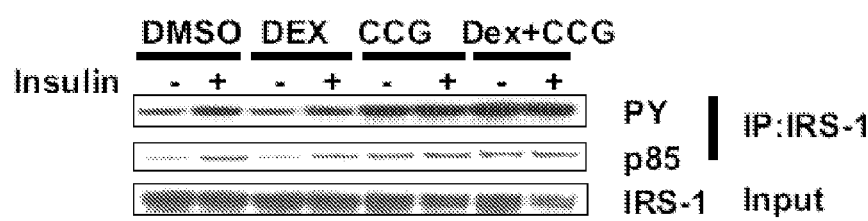
FIG. 11D is a phosphoimmunoblot showing that CCG-1423 increases basal and insulin-stimulated tyrosine phosphorylation of IRS-1 and its association with p85-PI 3-kinase, in both control and DEX-treated myotubes. * indicates $p<0.05$, $p<0.01$, *$p<0.001$.

In parallel, CCG-1423 enhanced insulin action in C2C12 myotubes. Overnight treatment with 1 μM CCG-1423 increased insulin-stimulated Akt phosphorylation, both in the presence and absence of dexamethasone (41% for both, p=0.01 and p=0.007, respectively), while having no effect on p42/44 ERK phosphorylation (FIG. 11C). This effect appeared to be mediated at the level of upstream insulin signals, as CCG-1423 increased both basal and insulin-stimulated tyrosine phosphorylation of IRS-1 protein and its association with the p85 regulatory subunit of PI 3-kinase (FIG. 11D), without altering p85 expression.

Figure 11E:
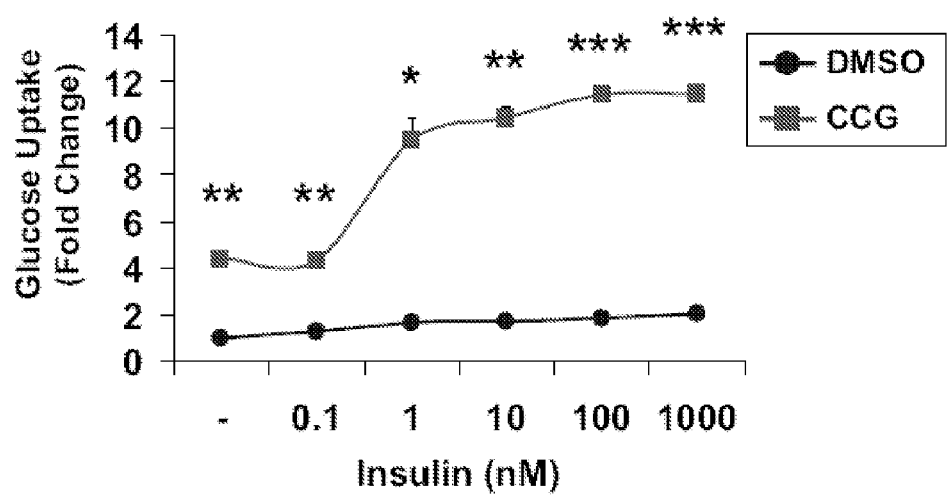
FIG. 11E is a line graph showing that both basal and insulin-stimulated 2-deoxyglucose uptake are increased by >4-fold in L6 myotubes following CCG-1423, with enhanced insulin sensitivity (1 μM, 16 hours). * indicates $p<0.05$, $p<0.01$, *$p<0.001$.

Since CCG-1423 increased insulin signalling in myotubes, we hypothesized that CCG-1423 might also enhance glucose uptake. In DMSO (vehicle)-treated myotubes, insulin stimulated a 2-fold increase in deoxyglucose uptake in a dose-dependent manner, consistent with prior reports and the low insulin responsiveness in cultured myotubes (FIG. 11E). However, in cells incubated with CCG-1423, glucose uptake was increased by 4-fold in the basal state, and the magnitude of the insulin-stimulated response was further increased (11.5-fold response at 1 μM insulin, FIG. 11E). In parallel, expression of the dominant glucose transporters GLUT4 and GLUT1 was increased by CCG-1423 treatment by 4.1 and 2.5 fold, respectively ($p<0.004$). Similar effects of CCG-1423 were observed in L6 myotubes.

The effects of CCG-1423 on human myotubes, and whether these effects would differ in myotubes derived from controls (n=2) vs. diabetic subjects (n=6), were also evaluated. Interestingly, the effects of CCG-1423 to promote basal increases in glucose uptake are substantially greater in diabetic subjects (mean 3.2-fold vs. 1.2-fold in control subjects). The differential responsiveness in subjects with DM supports the concept that SRF pathways are more robustly activated in humans with insulin resistance and DM, and therefore potentially more sensitive to SRF inhibition. Taken together, these results strongly suggest that CCG-1423-mediated decreases in SRF transcriptional activity can markedly enhance cellular metabolism at multiple levels, including increased IRS-1 tyrosine phosphorylation, Akt phosphorylation, and glucose uptake.

Example 6

Figure 12:
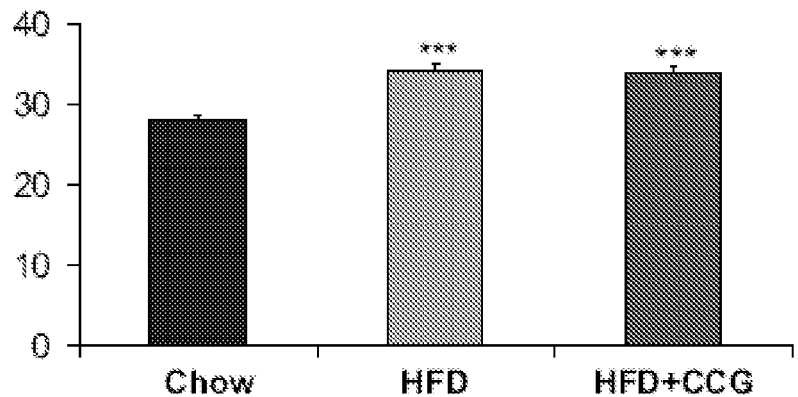
FIG. 12 is a bar graph demonstrating that body weight in obese, HFD-fed mice was not altered by CCG-1423 treatment.

Inhibition of SRF Activity Improves Insulin Sensitivity in Diet-Induced Obesity and Insulin Resistance Animal Models To examine the therapeutic potential of this SRF inhibitor in vivo, we assessed responses to CCG-1423 treatment in mice with diet-induced obesity. As expected, mice fed a high-fat diet (HFD) for 10 weeks had significantly elevated glucose as compared with chow-fed controls, under both fasting (96±4 vs. 66±2 mg/dl, HFD vs. chow) and fed (188±14 vs. 132±6 mg/dl) conditions, indicating that these DIO mice had developed insulin resistance. The HFD mice were administered CCG-1423 (0.15 mg/kg body weight intraperitoneally) for two weeks. No significant change in food intake or body weight (FIG. 12) was observed in comparison with vehicle-treated HFD mice. CCG-1423 treatment did not alter expression of SRF or ELK1. However, consistent with its effect to reduce SRF transcription, CCG-1423 treatment significantly decreased expression of SRF targets in skeletal muscle, e.g., ZYX and PDLIM7, as compared to vehicle-injected controls.

Figure 13A:
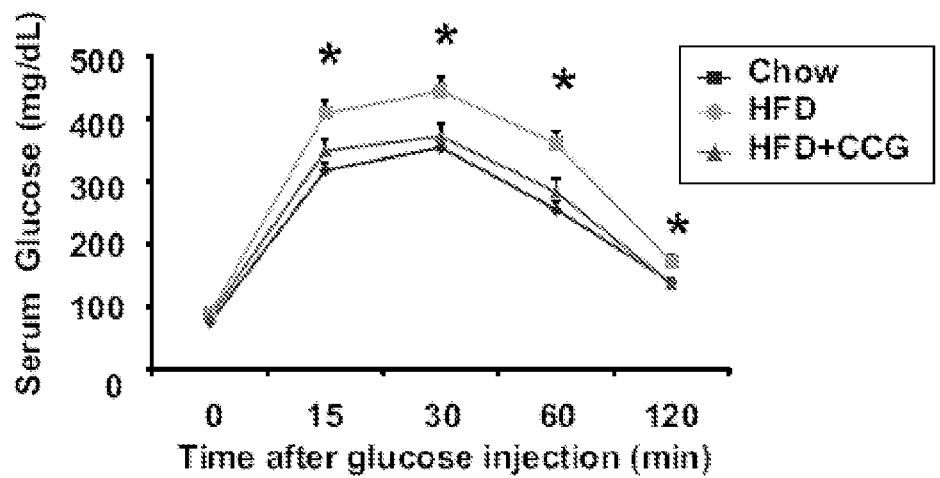
FIG. 13A is a line graph showing that glucose tolerance improves following in vivo CCG-1423 treatment in HFD-fed mice (HFD+CCG) compared to vehicle-treated HFD or chow-fed controls. * indicates $p<0.05$, $p<0.01$, *$p<0.001$.
Figure 13B:
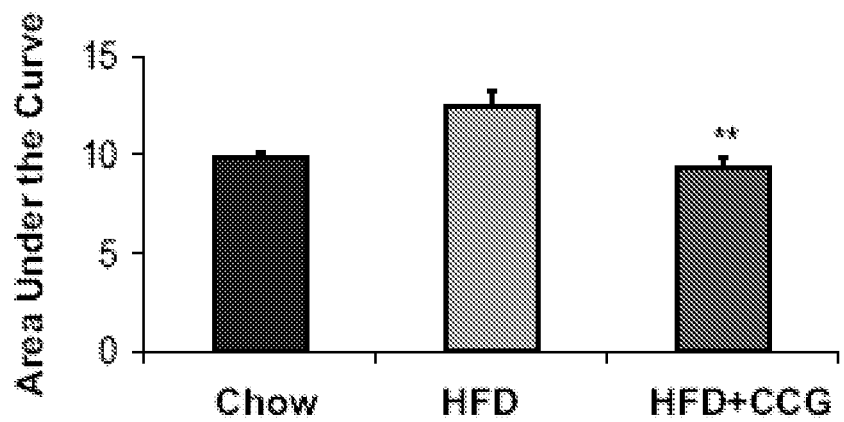
FIGS. 13B and 13C are bar graphs showing that area under the curve (AUC) and serum insulin levels during glucose tolerance test (15 minutes after glucose injection) (13C) were significantly reduced in CCG-1423 treated animals (HFD+CCG) compared to vehicle-treated HFD animals. * indicates $p<0.05$, **$p<0.01$.
Figure 13C:
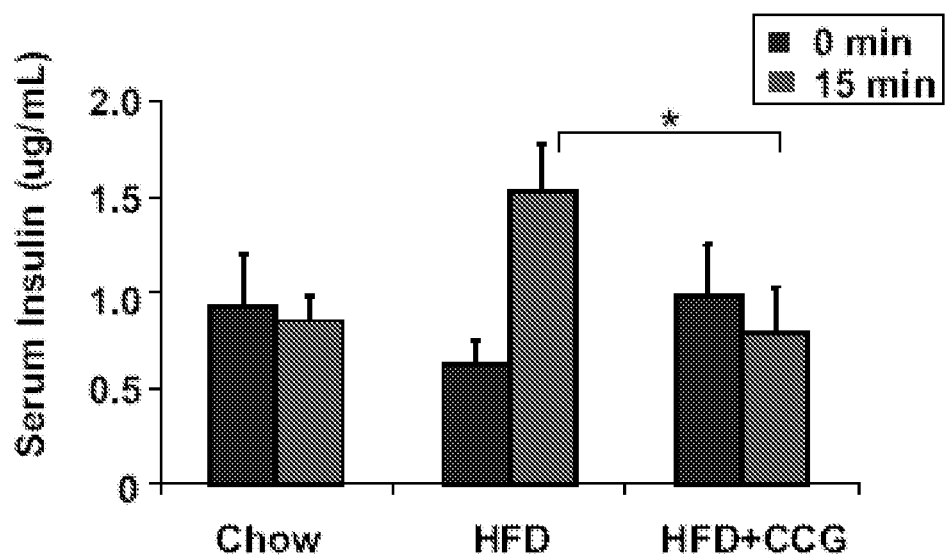

More importantly, in vivo glucose tolerance was significantly improved in HFD-fed mice treated with CCG-1423 as compared to HFD-fed vehicle-treated controls as evidenced by intra peritoneal glucose tolerance test (IGTT) or by intra peritoneal insulin tolerance test (ITT) (FIGS. 13A-B, $p<0.006$ for GTT AUC). In parallel, the high insulin levels associated with insulin resistance were normalized by CCG-1423 treatment (FIG. 13C). No differences in insulin tolerance testing, circulating fatty acid, or adiponectin levels were observed, suggesting the effect of CCG-1423 on glucose tolerance occurred, at least in part, via insulin-independent pathways.

Together, these results support the concept that strategies to reduce SRF transcriptional activity, e.g., using CCG-1423, may have beneficial effects to treat insulin resistance and type 2 diabetes.

Example 7

Increased Expression of SRF Target Genes and STARS in Humans at Risk for Diabetes To identify additional genes and pathways linked to DM2 and insulin resistance associated with diabetes family history, gene expression in quadriceps muscle biopsies was analyzed from 3 groups of human subjects: (1) normoglycemic individuals, without diabetes in any first-degree relative (FH−, n=15), (2) normoglycemic individuals, with diabetes in one or both parents (FH+, n=26), and (3) individuals with established type 2 diabetes (DM2, n=11). All subjects were metabolically characterized with intravenous glucose tolerance tests to assess insulin sensitivity ($S_1$; minimal model analysis; see Bergman et al., J Clin. Invest 79:790-800 (1987)). Family history subjects were normoglycemic and had normal HbAlc, and slightly, but not significantly higher body mass index (BMI), and were insulin resistant, as demonstrated by 50% higher fasting insulin levels and 41% lower $S_1$. Interestingly, STARS expression was increased by over 2-fold in skeletal muscle from human subjects with type 2 diabetes ($p<0.01$ vs. normoglycemic family history negative subjects). Subjects with established DM2 were even more insulin resistant, as indicated by 4-fold higher insulin levels and 66% lower $S_1$, and were hyperglycemic, with elevated fasting glucose and hemoglobin A1c.

Gene expression was assessed using high-density oligonucleotide arrays (Affymetrix U133 Plus 2.0), analyzing data on both an individual and pathway level. Consistent with previous studies, gene set enrichment analysis revealed significant reductions in pathways of genes involved in mitochondrial oxidative phosphorylation and fatty acid metabolism (FIG. 14). However, this pattern was not observed in normoglycemic FH+ insulin resistant subjects (FIG. 14), suggesting it is not related to the insulin resistance that precedes DM2 and is observed in first-degree relatives.

Example 8

Expression of MKL1-dependent SRF Target Genes is Increased in Human Type 2 DM and Insulin Resistance The top-ranking gene set enriched in both insulin resistant FH+ and DM2 subjects was a group of genes regulated by the transcription factor serum response factor (SRF) and its transcriptional coactivator megakaryocytic leukemia 1 (MKL1)

(normalized enrichment score 1.63, FDR 0.02 for DM vs. FH−, 0.73 for FH+ vs. FH−, FIG. 15A). This subset of SRF target genes is regulated by nuclear localization of MKL1 and includes genes related to the actin cytoskeleton and muscle differentiation. Indeed, quantitative PCR confirmed the microarray results, demonstrating 30-50% increases in expression of cytoskeleton-related SRF target genes, e.g. PDLIM7/enigma and vinculin (VCL), in both FH+ and DM2 human subjects (FIG. 15B). Upregulation of these MKL1-dependent SRF targets was also observed in C57/BL6 mice fed a high-fat diet; these patterns were normalized by treatment with the insulin sensitizer rosiglitazone (PCR expression data, FIG. 15C).

Figure 16:
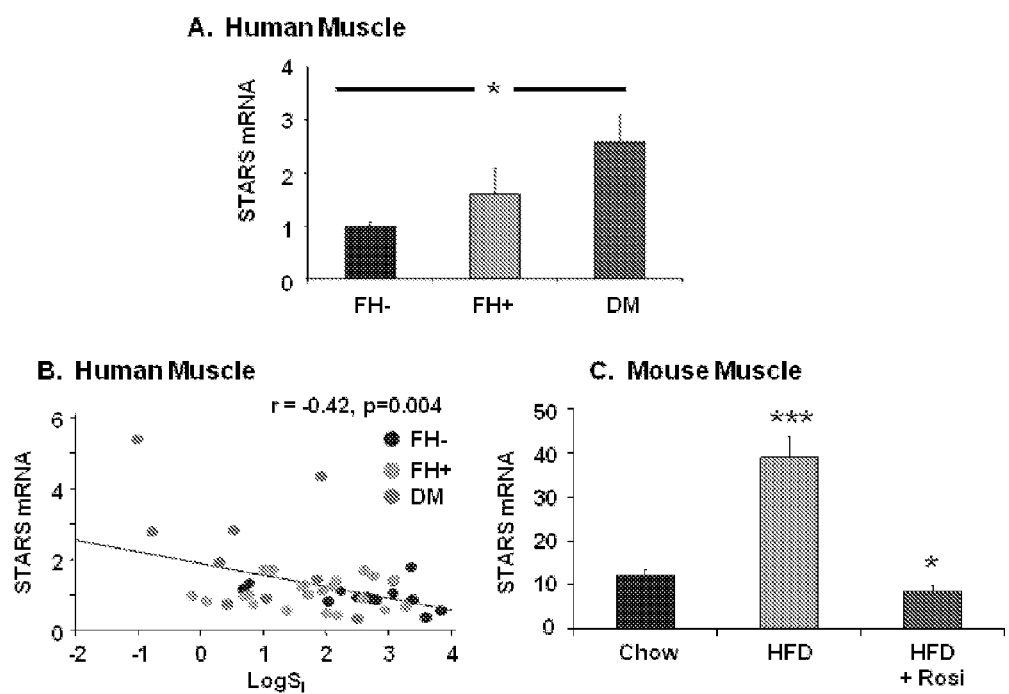
FIG. 16A is a bar graph demonstrating that expression of STARS is increased by 2.5 fold in type 2 diabetes and 1.6-fold in FH+ humans (ANOVA $p<0.05$, $p=0.03$ for FH− vs. DM in post-hoc testing).
FIG. 16B is a line graph demonstrating that expression of STARS is inversely correlated with insulin sensitivity (r=−0.42, p=0.004).
FIG. 16C is a bar graph demonstrating that STARS expression is increased 3-fold in C57BL/6J mice fed HFD and normalized by rosiglitazone (n=7-9/group).

To better understand the regulation of SRF target genes, the expression of individual genes was examined as a function of family history or presence of DM2. The top-ranking differentially expressed gene was striated muscle activator of Rho signaling (STARS, also known as ABRA), an activator of MKL1-dependent SRF transcription. Expression of STARS was increased by 2.5 fold in subjects with established DM2, with intermediate expression in FH+ subjects (FIG. 16A). While there was substantial interindividual variability within groups, STARS expression inversely correlated with insulin sensitivity across the entire human cohort (r=−0.42, p<0.004, FIG. 16B). STARS expression was also increased in mice made insulin resistant by high-fat feeding (3-fold, p<0.001, FIG. 16C). Thus, these data suggest that increased STARS expression may contribute to the increased MKL1-dependent SRF target gene expression observed in both humans and mice with insulin resistance.

Figure 17:
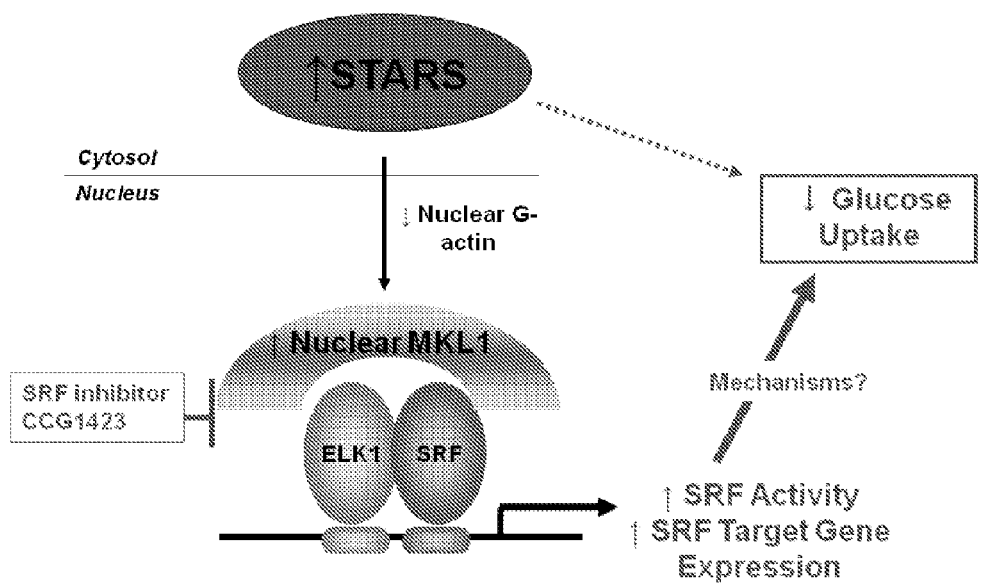
FIG. 17 is a schematic depicting a model of increased STARS expression, as observed in humans with diabetes family history and established DM2, reducing nuclear G-actin, leading to increased nuclear localization of MKL1, increased SRF transcriptional activity, SRF target gene expression, and reduced glucose uptake.

An L6 cell line stably expressing Myc-tagged STARS was generated via retroviral infection. In brief, a GFP-Myc-STARS retroviral vector (pMSCV-GFP vector backbone) was transfected into Phoenix cells. 48 hours later, the supernatant was collected, filtered (0.2μ), titered, mixed with 8 μg/mL of Polybrene, and added to L6 myoblasts which had been split 16 hours before the addition of retrovirus-containing media. L6 cells were harvested 48 hours later and GFP-expressing cells were selected using flow cytometry (Joslin Cell Cytometry Core). Using this protocol, cells stably expressing STARS were generated (24-fold at RNA level, 4-fold at protein level, FIG. 17). These cells, with stable expression of the Myc-GLUT4 construct, have enhanced responsiveness for glucose uptake and allow for immunohistochemical analysis of surface Myc-tagged GLUT4.

To determine whether increased expression of STARS can modulate glucose uptake, basal and insulin-stimulated glucose uptake in are measured in L6 myotubes overexpressing STARS (day 6 of differentiation). In brief, following overnight serum starvation, myotubes are treated with insulin (0 to 100 nM) for 20 minutes and then incubated with transport solution (140 mM NaCl, 20 mM Hepes, 5 mM KCl, 2.5 mM MgSO$_4$, 1.0 mM CaCl2, 10 μM 2-deoxyglucose, 0.5 μCi/mL [$^3$H]-2-deoxyglucose) for 10 minutes. Cells are lysed in 0.05N NaOH and radioactivity determined by scintillation counting. All assays are performed in quadruplicate and corrected by uptake in cytochalasin-treated wells. Glucose transport assays are also performed in STARS-Myc-GLUT4 cells, given their higher insulin responsiveness.

In parallel, GLUT4 translocation is assessed as a function of STARS expression in Myc-GLUT4 L6 myotubes (day 6) grown in 8-chamber slides (Lab-Tek II). Cells are incubated with serum-free medium overnight with anti-Myc antibody (1 μg/mL), stimulated with 100 nM insulin for 10 minutes, fixed (2% PFA), washed, incubated with Texas Red-conjugated anti-mouse IgG for 45 minutes, and mounted with DAPI-containing mounting medium (Vectashield®, Vector Laboratories, Burlingame, Calif.) for visualization using Olympus BX60 microscope.

In sum, the myotube model can be used to study gene-specific effects on basal and insulin-stimulated glucose uptake. The myotube model permits the determination of the effects of STARS expression on multiple aspects of cellular metabolism and pathway-specific insulin action, experiments not feasible in in vivo studies.

Example 9

Downregulation of STARS and SRF Pathway Activation Improves Glucose Uptake

Figure 19:
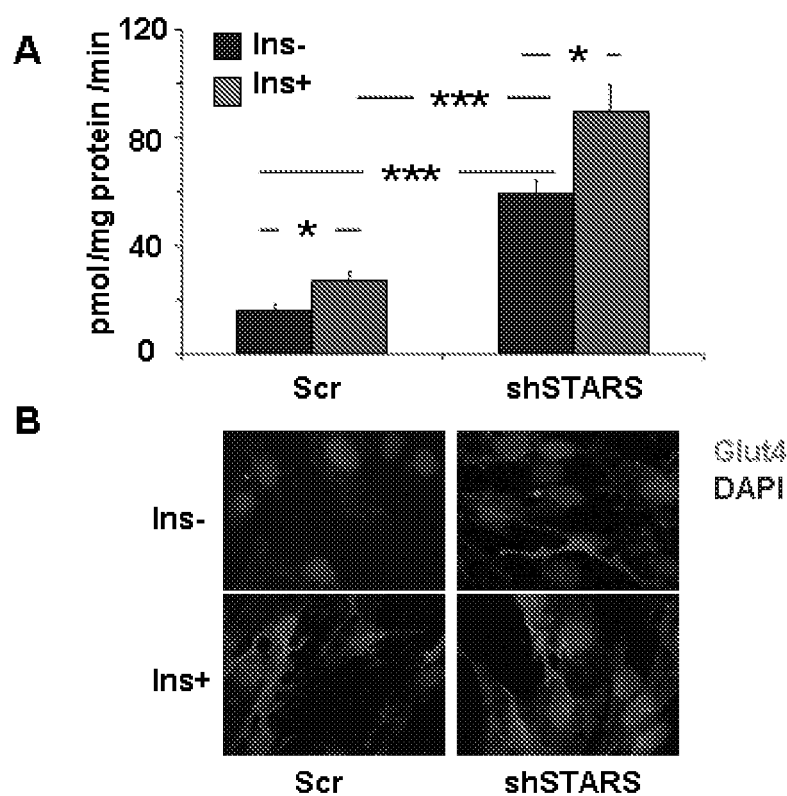
FIG. 19A is a bar graph demonstrating that shRNA-mediated reduction in STARS expression in Myc-GLUT4-L6 myocytes increases basal and insulin-stimulated glucose uptake (myotubes).
FIG. 19B is an image showing increased Myc-GLUT4 surface expression in both basal and insulin-stimulated conditions (anti-Myc IHC, myoblasts).

To address whether STARS and MKL1-dependent SRF transcriptional activity contribute to the pathophysiology of insulin resistance, experiments were performed to test whether modulation of STARS expression and/or SRF activation can improve key cellular phenotypes associated with insulin resistance, including insulin action and glucose uptake. L6 myotubes stably expressing Myc-GLUT4 were infected with an adenovirus containing a short hairpin targeting STARS, resulting in a 54% reduction in STARS protein expression; this was associated with a 3.7-fold increase in basal glucose uptake and a 3.6-fold increase in insulin-stimulated glucose uptake (FIG. 19A). Expression of GLUT1 and GLUT4 did not differ with STARS knockdown. However, STARS knockdown resulted in increased surface GLUT4 expression in both the basal (FIG. 19B, INS−, top right) and insulin-stimulated states (INS+, bottom right), in contrast to the scrambled control. Thus, these data indicate that reduction in STARS expression can enhance GLUT4 localization and glucose uptake—key phenotypes for cellular insulin sensitivity.

Figure 18:
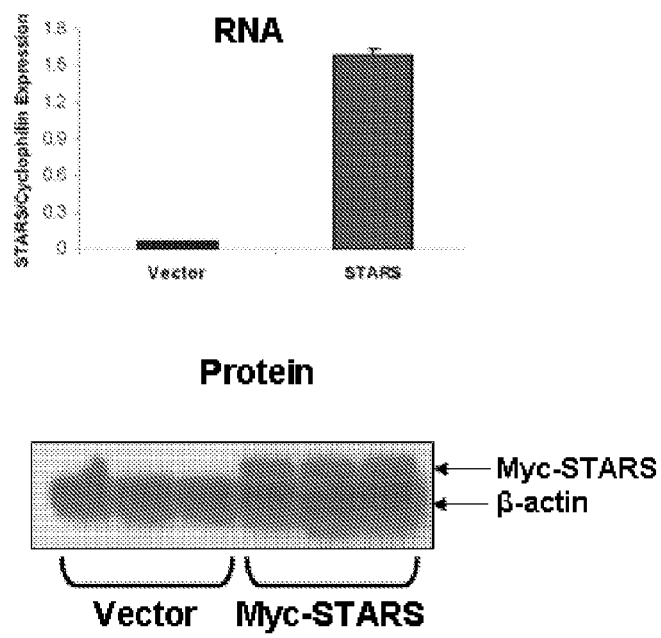
FIG. 18 contains a bar graph and an image showing stable expression of STARS in GFP-Myc-STARS L6 myoblasts ($p<0.001$ vs. vector) at RNA (upper) and protein (lower) level.

To test the effect of reduced STARS expression (shRNA) and reduced SRF pathway activation (chemical inhibitor CCG-1423) in cultured myotubes, knock-down assays were performed. shSTARS target sequences (Forward 5'-GATC-CCCCTGTAA GGCCCATCGGAAATTCAAGAGATTTC-CGATGGGCCTTACAGTTTTTGGAA A-3' (SEQ ID NO:1); Reverse 5'-AGCTTTTCCAAAAACTGTAAGGC-CCATCGG AAATCTCTTGAA TTTCCGATGGGCCTTA-CAGGGG-3' (SEQ ID NO:2)), or scrambled control (IDT RNA design), were cloned into pAdTrack-CMV adenoviral vector, and Myc-GLUT4 L6 myotubes were infected with amplified adenovirus (8×10$^7$ pfu/well, 6-well plate) at 3 days after differentiation. As detailed above, STARS expression was successfully reduced (>50%) at both an RNA and protein level (FIG. 18). Thus, experimental reductions in STARS expression are associated with an increase insulin signaling and basal glucose uptake in cultured myotubes.

Figure 20:
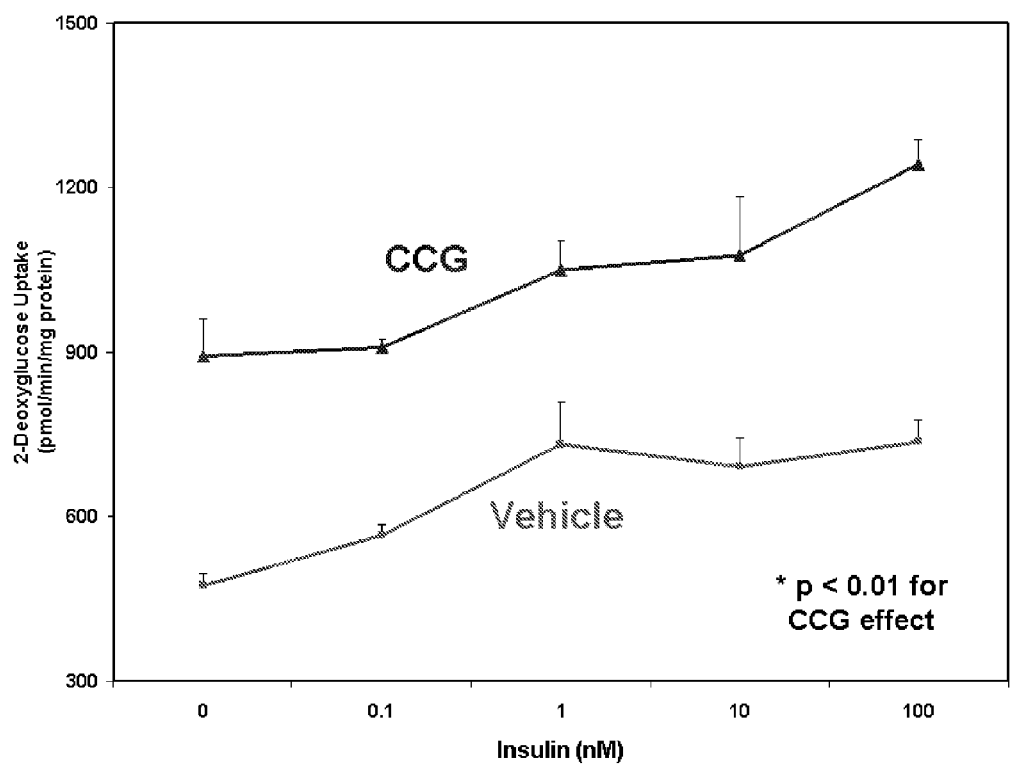
FIG. 20 is a line graph showing that CCG-1423 increases basal and insulin-stimulated 2-deoxyglucose uptake. Effects of CCG-1423 are significant at all insulin doses but * have been eliminated for clarity.

Since genetic knockdown of STARS expression enhanced glucose transport, a key question is whether pharmacologic inhibition of SRF transcriptional activity would similarly modulate glucose transport. Studies with CCG-1423, an SRF transcriptional inhibitor identified by compound library screening, were performed. CCG-1423 reduces SRE promoter activity in myotubes; these effects appear to be mediated, at least in part, by CCG-1423 inhibition of MKL1 nuclear localization. Interestingly, CCG-1423 treatment (1 μM, 16 hours) in Myc-GLUT4 L6 myotubes increased basal glucose uptake by 1.9-fold (p<0.02). By comparison, insulin stimulated glucose uptake by 1.6-fold (p<0.01; FIG. 20). The combination of CCG-1423 and insulin potently increased glucose uptake, by 2.6-fold (p<0.001 vs. insulin alone). These data using both siRNA and chemical inhibition strategies suggest that downregulation of STARS and SRF pathway activation can improve glucose uptake.

Example 10

In Vivo Reduction of STARS Expression Promotes Resistance to High Fat Diet

Given the interesting patterns of STARS expression in both human and animal models of insulin resistance, it is important to determine whether STARS contributes to the pathophysiology of insulin resistance. Thus, the physiological effects of altered STARS expression in vivo were determined using mice null for STARS. STARS-null mice were previously created. See Kuwahara et al., Mol Cell Biol 25:3173-3181 (2005). Mice were generated by insertion of a neomycin resistance cassette via homologous recombination, creating a stop codon within exon 1 (FIG. 21). Mice are born at the expected Mendelian ratio, with normal birth weight and normal patterns of early growth and development.

Metabolic phenotypes were observed in a pilot cohort of female mice (WT n=4, KO n=3 per group, age 12 months) fed a high fat diet for 4 months. Several striking phenotypes were observed: (1) Reduced body weight and total and abdominal fat mass (FIG. 22A, B), with no change in lean body mass (FIG. 22B) or food intake; (2) Increased whole-body energy expenditure (CLAMS), with reduced respiratory quotient during fasting, suggesting enhanced lipid oxidation (FIG. 22C, D): (3) Normal fasting glucose despite 42% reduction in fasting insulin level, suggesting enhanced insulin sensitivity (FIG. 23A, left and right); and (4) Improved glucose tolerance (FIG. 23B). In spite of the small cohort and single gender of the mice, these data are of great interest as they suggest that reduction in STARS results in resistance to high fat diet, potentially due to enhanced energy expenditure and altered fuel utilization, with improvements in glucose tolerance.

Figure 24:
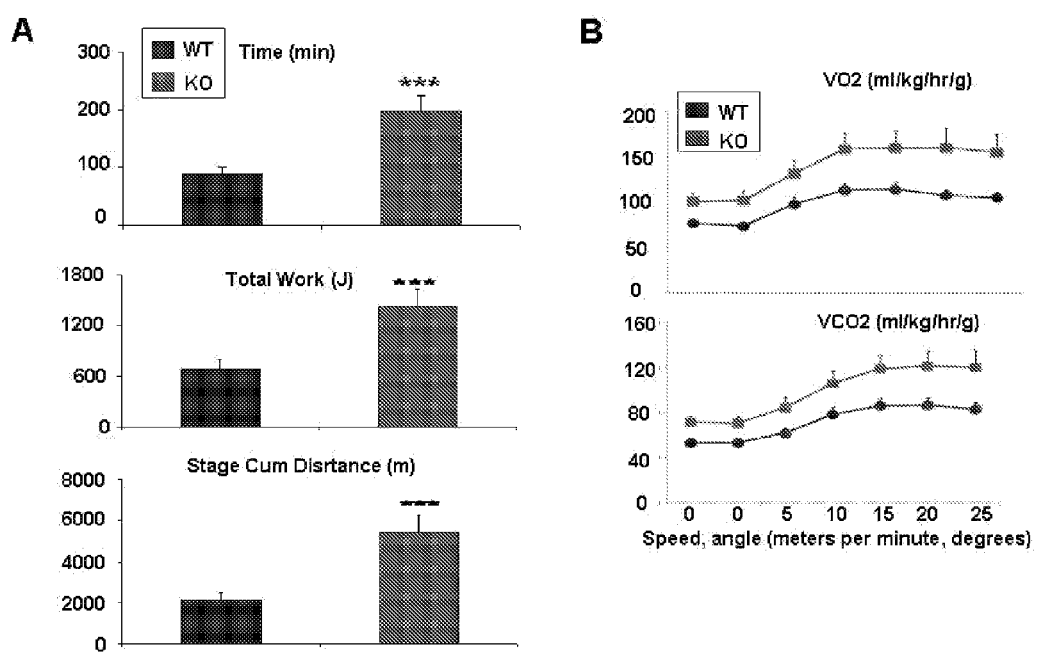
FIGS. 24A and 24B are graphs showing increased exercise capacity in STARS-null mice.

It has been observed that STARS deficient mice (STARS KO) are resistant to high fat diet-induced weight gain, with reduced adipose tissue accretion, but unchanged lean body mass. Furthermore, STARS KO mice have a 44% increase in basal energy expenditure (p<0.05 vs. wild type) and reduced respiratory quotient (RQ 0.76 vs. 0.78 for WT, p<0.001), indicating preferential utilization of lipids as energy source. In addition, skeletal muscle from STARS-null mice is more oxidative, as demonstrated by increased SDH staining. Consistent with increased oxidative capacity, STARS-null mice ran >2 times longer than WT mice (686.5±113.8 vs. 1621.5±82.2 joule, p<0.001) (FIG. 24A), with increased $VO_2$ max (7107±337 vs. 6077±115 ml/kg/hr, p<0.05) (FIG. 24B). This phenotype appears linked to enhanced fatty acid oxidation, as shRNA-mediated knock down of STARS expression in myotubes increased fatty acid oxidation by 13% (p<0.05).

These effects of STARS on systemic metabolism may be mediated at a cellular level by STARS inhibition of $Ca^{2+}$-dependent oxidative pathways, as overexpression of STARS inhibits MEF2- and calcineurin-dependent expression of the oxidative fiber type-specific marker troponin 1 (TNN1). Together, these data indicate that STARS is a key modulator of whole-body energy expenditure and exercise performance via regulation of muscle oxidative capacity, and suggest that modulation of the STARS-SRF signaling pathway may be beneficial for treatment of insulin resistance and type 2 diabetes.

Example 11

Figure 25:
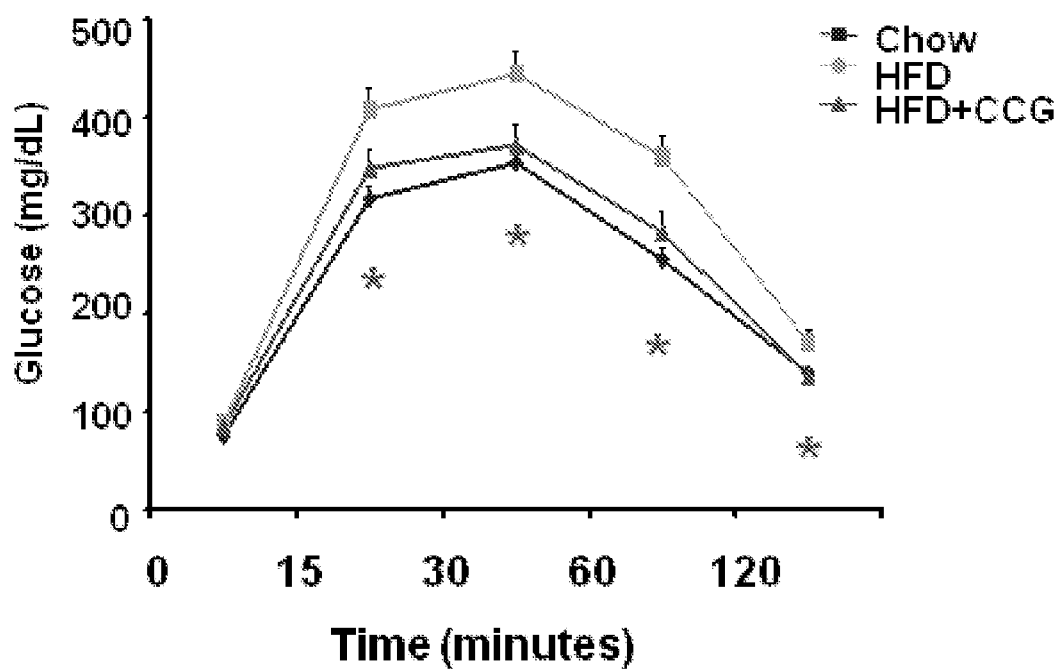
FIG. 25 is a line graph showing that CCG-1423 treatment for 2 weeks improves glucose tolerance in mice fed a high-fat diet (HFD+CCG line) as compared with mice fed HFD alone (HFD line).

SRF Pathway Activation is a Potential Therapeutic Target for Pharmacologic Modulation in Insulin Resistance Data presented herein suggest that SRF pathway activation may be a potential therapeutic target for pharmacologic modulation in insulin resistance. To test this hypothesis, mice are treated with CCG-1423 in 2 models of murine insulin resistance: (1) high-fat diet-fed C57BL/6J mice (60% of calories from fat), or (2) genetically obese ob/ob mice. For these studies, mice are injected with CCG-1423 0.15 mg/kg/day or vehicle (DMSO), intraperitoneally, for 2 weeks. Body weight and food intake are monitored daily. As demonstrated in FIG. 25, glucose tolerance in HFD-fed mice treated with CCG-1423 for 2 weeks was significantly improved with the GTT of normal chow-fed animals. In parallel, fed insulin levels were reduced by 50% by CCG-1423 as compared with HFD-fed mice (p<0.05), suggesting protection from HFD-induced insulin resistance. It is important to note that no differences in body weight or food intake were observed between groups. These data suggest that pharmacological targeting of the SRF pathway may be therapeutically beneficial.

ADDITIONAL REFERENCES

Shoelson et al., J Clin Invest 116, 1793-1801 (2006).
Tomas et al., J Cell Sci 119, 2156-2167 (2006).
Sun et al., Genome Res. 16, 197-207 (2006).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for improving glycemic control in a subject in need thereof, the method comprising administering a therapeutically effective amount of an inhibitor of MLK1-dependent SRF transcriptional activity.

2. The method of claim 1, wherein the inhibitor of MLK1-dependent SRF transcriptional activity is selected from the group consisting of small molecule inhibitors of STARS, dominant negatives targeting STARS, and inhibitory nucleic acids targeting STARS.

3. The method of claim 2, wherein the inhibitory nucleic acid targeting STARS is a small interfering RNA.

4. The method of claim 1, wherein the subject has, or is at risk of developing, insulin resistance or type 2 diabetes mellitus.

5. The method of claim 1, wherein the subject has metabolic syndrome.

6. The method of claim 1, wherein the subject is, or is at risk of becoming, obese.

* * * * *

UNITED STATES PATENT AND TRADEMARK OFFICE
CERTIFICATE OF CORRECTION

PATENT NO. : 8,815,799 B2
APPLICATION NO. : 13/701082
DATED : August 26, 2014
INVENTOR(S) : Mary Elizabeth Patti, Wanzhu Jin and Allison B. Goldfine Page 1 of 1

It is certified that error appears in the above-identified patent and that said Letters Patent is hereby corrected as shown below:

In the Specification

Column 1, line 24, the term "MLK1", should read --MKL1--.

Column 1, line 54, the term "MLK1", should read --MKL1--.

Column 1, line 56, the term "MLK1", should read --MKL1--.

Column 1, line 58, the term "MLK1", should read --MKL1--.

Column 1, line 67, the term "MLK1", should read --MKL1--.

Column 2, line 3, the term "MLK1", should read --MKL1--.

Column 2, line 13, the term "MLK1", should read --MKL1--.

In the Claims

Claim 1, column 29, line 23, the term "MLK1", should read --MKL1--.

Claim 2, column 29, line 25, the term "MLK1", should read --MKL1--.

Signed and Sealed this
Seventh Day of April, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
```

```
gatcccctg taaggcccat cggaaattca agagatttcc gatgggcctt acagtttttg    60
gaaa                                                                64

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agcttttcca aaaactgtaa ggcccatcgg aaatctcttg aatttccgat gggccttaca    60
gggg                                                                64
```